United States Patent [19]

Woodle et al.

[11] Patent Number: 5,356,633

[45] Date of Patent: Oct. 18, 1994

[54] METHOD OF TREATMENT OF INFLAMED TISSUES

[75] Inventors: Martin C. Woodle, Menlo Park; Francis J. Martin, San Francisco; Shi K. Huang, Castro Valley, all of Calif.

[73] Assignee: Liposome Technology, Inc., Menlo Park, Calif.

[21] Appl. No.: 958,100

[22] Filed: Oct. 7, 1992

Related U.S. Application Data

[63] Continuation-in-part of Ser. No. 642,321, Jan. 15, 1991, Pat. No. 5,213,804, which is a continuation-in-part of Ser. No. 425,224, Oct. 20, 1989, Pat. No. 5,013,556.

[51] Int. Cl.$^5$ ............ A61K 9/127; A61K 37/22
[52] U.S. Cl. ............ 424/450; 424/423; 424/426; 514/886; 514/863
[58] Field of Search ............ 424/450, 423, 424

[56] References Cited

U.S. PATENT DOCUMENTS

| | | | |
|---|---|---|---|
| 3,993,754 | 11/1976 | Rahman et al. | 514/12 |
| 4,426,330 | 1/1984 | Sears | 554/80 |
| 4,534,899 | 8/1985 | Sears | 554/80 |
| 4,797,285 | 1/1989 | Barenholz et al. | 424/450 |
| 4,837,028 | 6/1989 | Allen et al. | 424/450 |
| 4,863,739 | 9/1989 | Perez-Solar et al. | 424/450 |
| 4,904,479 | 2/1990 | Illum | 424/490 |
| 4,920,016 | 4/1990 | Allen et al. | 424/450 |
| 4,962,022 | 10/1990 | Fleming et al. | 424/450 |
| 5,013,556 | 5/1991 | Woodle et al. | 424/450 |
| 5,213,804 | 5/1993 | Martin et al. | |

FOREIGN PATENT DOCUMENTS

WO90/00389 1/1990 PCT Int'l Appl. .
WO91/05545 5/1991 PCT Int'l Appl. .

OTHER PUBLICATIONS

Love, W. G., et al., "Specific accumulation of cholesterol-rich liposomes in the inflammatory tissue of rats with adjuvant arthritis," *Ann. Rheum. Dis.* 49(8):611-614 (1990).

Love, W. G., et al., "Specific accumulation of technetium-99m radiolabelled, negative liposomes in the inflamed paws of rats with adjuvant induced arthritis: effect of liposome size," *Ann. Rheum. Dis.* 48:143-148 (1989).

Williams, B.D., et al., "Synovial accumulation of technetium labelled liposomes in rheumatoid arthritis," *Ann. Rheum. Dis.* 46:314-318 (1987).

Lasic, D. D., et al., "On the Molecular Mechanism of Steric Stabilization of Liposomes in Biological Fluids,'-'*Journal of Liposome Research* 2(3): 335-353 (1992).

*Primary Examiner*—Thurman K. Page
*Assistant Examiner*—James M. Spear
*Attorney, Agent, or Firm*—Carol A. Stratford; Peter J. Dehlinger

[57] ABSTRACT

A method of and composition for concentrating a therapeutic agent in an inflamed dermal region are disclosed. The composition, which is also used in the method, is a liposomal composition. The liposomes contain the therapeutic agent in entrapped form and are composed of vesicle-forming lipids including a vesicle-forming lipid derivatized with hydrophilic biocompatible polymer. After intravenous administration, the liposomes are taken up by the inflamed region within 24-48 hours, for site-specific release of entrapped compound into the inflamed region.

6 Claims, 14 Drawing Sheets

METHOD OF TREATMENT OF INFLAMED TISSUES

This application is a continuation-in-part of application Ser. No. 642,321, filed Jan. 15, 1991, now U.S. Pat. No. 5,213,804 which is a continuation-in-part of U.S. patent application Ser. No. 425,224, now U.S. Pat. No. 5,013,556, filed Oct. 20, 1989.

FIELD OF THE INVENTION

The present invention relates to a liposome composition and method, particularly for use in concentrating therapeutics at sites of inflammation in the body.

REFERENCES

Allen, T. M., (1981) *Biochem. Biophys. Acta* 640: 385–397.

Allen, T. M., and Everest, J. (1983) *J. Pharmacol. Exp. Therap.* 226: 539–544.

Ashwell, G., and Morell, A. G. (1974) *Adv. Enzymology* 41: 99–128.

Bartlett, G. R. (1959) *J. Biol. Chem.* 234:466–468.

Czop, J. K. (1978) *Proc. Natl. Acad. Sci. USA* 75:3831.

Durocher, J. P., et al. (1975) *Blood* 45:11.

Ellens, H., et al. (1981) *Biochim. Biophys. Acta* 674: 10–18.

Engelberg, I. and Kohn, J. (1991) *Biomaterials* 12: 292–304.

Gilman, A. G. et al., eds. (1990) *The Pharmacological Basis of Therapeutics* (Eighth Edition) Pergamon Press, New York.

Gabizon, A., Goren, D. and Barenholz, Y. (1988) *Israel J. Med. Sci.* 24: 512–517.

Gabizon, A., Huberty, J., Straubinger, R. M., Price, D. C. and Papahadjopoulos, D. (1988-1989) *J. Liposome Res.* 1: 123–135.

Gabizon, A., Shiota, R. and Papahadjopoulos, D. (1989) *J. Natl. Cancer Inst.* 81: 1484–1488.

Greenberg, J. P., et al. (1979) *Blood* 53: 916.

Gregoriadis, G., and Neerunjun, D. (1974) *Eur. J. Biochem.* 47: 179–185.

Gregoriadis, G., and Senior, J. (1980) *FEBS Lett.* 119: 43–46.

Hakomori, S. (1981) *Ann. Rev. Biochem.* 50: 733–764.

Haynes, Jr. R. C. (1990) in Gilman, A. G. et al., eds. (1990) *The Pharmacological Basis of Therapeutics* (Eighth Edition) Pergamon Press, New York, pp 1431–1462.

Huang, S. K., et al. (1991) *Biochim. Biophys. Acta* 1069(1): 117–121.

Hwang, K. J., et al. (1980) *Proc. Natl. Acad. Sci. USA* 77: 4030.

Jonah, M. M., et al. (1975) *Biochem. Biophys. Acta* 401: 336–348.

Juliano, R. L., and Stamp, D. (1975) *Biochem. Biophys. Res. Commun.* 63: 651–658.

Kadison, P. et al. (1988) In: *Inflammation: Basic Principles and clinical Correlates*, ed. by Gallin, J. A., et al, Raven Press, N.Y.

Karlsson, K. A. (1982) In: *Biological Membranes*, Vol. 4, D. Chapman (ed.) Academic Press, N.Y., pp. 1–74.

Kimelberg, H. K., et al. (1976) *Cancer Res.* 6: 2949–2957.

Kirby, C. J. and Gregoriadis (1984) In: *Liposome Technology*, Vol. 3, G. Gregoriadis (ed.) CRC Press, Boca Raton, Fla., p. 19.

Lopez-Berestein, G., et al. (1984) *Cancer Res.* 44: 375–378.

Martin, F. J. (1990) In: *Specialized Drug Delivery Systems—Manufacturing and Production Technology*, P. Tyle (ed.) Marcel Dekker, New York, pp. 267–316.

McDonald, D. M. (1988) *J. Neurocytol.* 17: 583–603.

Niwa, Y. (1989) *Dermatologica* 179(suppl. 1): 101–106.

Okada, N. (1982) *Nature* 299: 261.

Olson, F., et al., *Eur. J. Cancer,* 18: 167–176 (1982).

Papahadjopoulos, D., et al., "Sterically Stabilized Liposomes: Improvements in Pharmacokinetics and Anti-Tumor Therapeutic Efficacy", *PNAS*, 88: 11460–11464.

Papenfuss, H. D., et al. (1979) *Microvascular Res.* 18: 311–318.

Pincelli, C. et al. (1992) *J. Invest. Dermatol.* 98: 421–427.

Poste, G., et al., in *Liposome Technology* Volume 3, page 1 (Gregoriadis, G., et al, eds.), CRC Press, Boca Raton (1984).

Richardson, V. J., et al. (1979) *Br. J. Cancer* 40: 3543.

Schauer, R. (1982) *Adv. Carbohydrate Chem. Biochem.* 40: 131.

Scherphof, T., et al. (1978) *Biochim. Biophys. Acta* 542, 296–307.

Senior, J., and Gregoriadis, G. (1982) *FEBS Lett.* 145: 109–114.

Senior, J., et al. (1985) *Biochim. Biophys. Acta* 839: 1–8.

Sundberg, J. P., et al., *J. Investigative Dermatology* 95(5): 615–635 (1990).

Szoka, F., Jr., and Papahadjopoulos, D., *Proc. Natl. Acad. Sci. USA* 75(9): 145–1497 (1978).

*The Physician's Desk Reference,* (1992) Medical Economics Company, Oradell, N.J.

Woodle, M. C., et al., (1990). "Improved long-circulating (Stealth®) Liposomes using synthetic liposomes", *Proceed. Intern. Symp. Control. Rel. Bioact. Mater.*, 17:77.

Woodle, M. C., et al., (1991). "In Vivo Studies of Long Circulating (Stealth®) Liposomes in Rats", *Period Biol.*, 93: 349.

Woodle, M. C. et al. (1992) *Pharm. Res.* 9: 260–265.

Woodruff, J. J., et al. (1969) *J. Exp. Med.* 129: 551.

Wu, N. Z., and Dewhirst, M. W. (1991) "Measuring tissue uptake of intravenously injected using macromolecules using fluorescence video microscopy", Microvascular Res., Louisville, Ky.

BACKGROUND OF THE INVENTION

The inflammatory process is a sequence of physiological events which can be elicited by numerous stimuli, including infectious agents, ischemia, antigen-antibody interactions, and thermal or other injurious insults. Although the sequence of events constituting an inflammatory reaction may vary according to the nature and location of the eliciting insult, there are certain events common to most inflammatory reactions. These include, in the acute phase, vasodilation, resulting in increased blood flow to the inflamed region and increased capillary permeability. This phase is followed by an increase in fluid in the region (edema) and movement of blood leukocytes and, finally, phagocytes from the blood vessels to the region.

It would be desirable, for treatment of inflamed tissues or regions, to target therapeutic compounds selectively to the region via the bloodstream. Site-specific targeting would be particularly helpful in reducing toxic side effects and in increasing the dose of drug which can safely be delivered to an inflamed region.

Liposomes have been proposed as a drug carrier for intravenously (IV) administered compounds, including both imaging and therapeutic compounds. However, the use of liposomes for site-specific targeting via the bloodstream has been severely restricted by the rapid clearance of liposomes by cells of the reticuloendothelial system (RES). Typically, the RES will remove 80–95% of a dose of IV injected liposomes within one hour, effectively outcompeting the selected target site for uptake of the liposomes.

A variety of factors which influence the rate of RES uptake of liposomes have been reported (e.g., Gregoriadis, 1974; Jonah; Gregoriadis, 1972; Juliano; Allen, 1983; Kimelberg, 1976; Richardson; Lopez-Berestein; Allen, 1981; Scherphof; Gregoriadis, 1980; Hwang; Patel, 1983; Senior, 1985; Allen, 1983; Ellens; Senior, 1982; Hwang; Ashwell; Hakomori; Karlsson; Schauer; Durocher; Greenberg; Woodruff; Czop; and Okada). Briefly, liposome size, charge, degree of lipid saturation, and surface moieties have all been implicated in liposome clearance by the RES. However, no single factor identified to date has been effective to provide long blood halflife, and more particularly, a relatively high percentage of liposomes in the bloodstream 24 hours after injection.

In addition to a long blood halflife, effective drug delivery to an inflamed site would also require that the liposomes be capable of penetrating the continuous endothelial cell layer and underlying basement membrane surrounding the vessels supplying blood to the region. A characteristic of local inflammation is a general, acute increase in permeability of the vasculature to proteins in the region of the inflammation, followed by migration of neutrophils out of the bloodstream into the inflamed region. However, neither of these events predicts the ability of liposomes to pass through the epithelial cell barriers and adjacent basement membrane, since proteins are generally much smaller than liposomes, and neutrophils possess specific binding sites and active mechanisms for penetrating the blood vessels.

In fact, studies reported to date indicate that even where the permeability of blood vessels increases, extravasation of conventional liposomes through the vessels does not increase significantly (Poste). Based on these findings, it was concluded that although extravasation of liposomes from capillaries compromised by disease may be occurring on a limited scale below detection levels, its therapeutic potential would be minimal (Poste).

SUMMARY OF THE INVENTION

One general object of the invention is to provide a method which is effective to concentrate a therapeutic compound in an inflamed region in a subject.

The invention includes, in one aspect, a method for concentrating a therapeutic compound in an inflamed dermal region. The method includes administering to the subject, by parenteral injection, a composition of liposomes. The liposomes of the composition are (i) composed of vesicle-forming lipids including an amphipathic vesicle-forming lipid derivatized with a hydrophilic biocompatible polymer of a size and in a molar amount effective to extend liposome blood circulation time, measured 24 hours after administration, severalfold and over that circulation time achievable in the absence of the hydrophilic polymer, (ii) of a selected mean particle diameter in the size range between about 0.07–0.20 microns, and (iii) contain in liposome-entrapped form, a therapeutic compound effective against the source of the inflammation. The method includes concentrating the liposomes in the inflamed region, and by such concentrating, concentrating liposome-entrapped compound in the inflamed region.

In a preferred embodiment, the hydrophilic biocompatible polymer is a polyethylene glycol having a molecular weight between about 300 and 5,000 daltons. In another preferred embodiment the polymer is selected from the group consisting of polyglycolic acid (PGA), polylactic acid (PLA), a copolymer of PGA and PLA, and polyvinyl alcohol.

For use in treatment of dermal inflammation, the liposome-entrapped compound in one embodiment is a steroidal anti-inflammatory compound. In a related embodiment, the antiinflammatory compound is selected from the group consisting of prednisone, methylprednisolone, paramethazone, 11-fludrocortisol, triamcinolone, betamethasone and dexamethasone. In yet another embodiment, the liposome entrapped compound is beclomethasone.

In a related embodiment, for use in treating a psoriatic dermal inflammation the liposome-entrapped compound is selected from the group consisting of steroidal antiinflammatory agents, non-steroidal antiinflammatory agents, methotrexate, azaribine, etretinate, anthralin, psoralins, and immunosuppressants such as cyclosporine.

In another aspect, the invention includes an injectable liposome composition for use in a method of treating an inflamed dermal region. The liposome composition is characterized as follows: (a) composed of vesicle-forming lipids including an amphipathic vesicle-forming lipid derivatized with a hydrophilic biocompatible polymer of a size and in a molar amount effective to extend liposome blood circulation time, measured 24 hours after injection, severalfold and over that circulation time achievable in the absence of the hydrophilic polymer, (b) liposomes having a selected mean particle diameter in the size range between about 0.07–0.20 microns, (c) containing in liposome-entrapped form, a therapeutic compound effective against the source of inflammation, and (d) ability to accumulate selectively in the inflamed tissue following parenteral administration, thereby to concentrate liposome-entrapped compound at the site of inflammation.

In a preferred embodiment, the hydrophilic polymer of the liposome composition is a polyethyleneglycol having a molecular weight between about 300–5,000 daltons. In yet another preferred embodiment, the hydrophilic polymer is selected from the group consisting of polyglycolic acid (PGA), polylactic acid (PLA), a copolymer of PGA and PLA, and polyvinyl alcohol.

In another preferred embodiment of the invention, the liposome composition includes a therapeutic compound is a steroidal anti-inflammatory agent. In yet a further preferred embodiment, the therapeutic compound is selected from the group consisting of prednisone, methylprednisolone, paramethazone, 11-fludrocortisol, triamcinolone, betamethasone and dexamethasone. In another embodiment, the therapeutic compound is beclomethasone.

For use in treatment of inflammation associated with psoriasis, the therapeutic compound in one embodiment is selected from the group consisting of steroidal antiinflammatory agents, non-steroidal antiinflammatory agents, methotrexate, azaribine, etretinate, anthralin, psoralins, and immunosuppressants such as cyclosporine.

The invention also includes, in yet another related aspect, a method of preparing an anti-inflammatory agent for localization in an inflamed dermal region, after parenteral injection. The method includes entrapping the agent in liposomes which are characterized by: (a) composed of vesicle-forming lipids including an amphipathic vesicle-forming lipid derivatized with a hydrophilic biocompatible polymer of a size and in a molar amount effective to extend liposome blood circulation time, measured 24 hours after injection of the composition, severalfold and over that achievable in the absence of the hydrophilic polymer, (b) liposomes having a selected mean particle diameter in the size range between about 0.07–0.20 microns, (c) containing in liposome-entrapped form, an antiinflammatory agent effective against the source of the inflammation, and (d) ability to accumulate selectively in the inflamed tissue following parenteral administration, thereby to concentrate liposome-entrapped agent at the site of inflammation.

In a preferred embodiment of the preparation method, the hydrophilic biocompatible polymer is a polyethylene glycol having a molecular weight between about 300 and 5,000 daltons.

In yet another preferred embodiment, the hydrophilic biocompatible polymer is selected from the group consisting of polyglycolic acid (PGA), polylactic acid (PLA), a copolymer of PGA and PLA, and polyvinyl alcohol.

In still another preferred embodiment, the liposome-entrapped antiinflammatory agent is a steroidal antiinflammatory compound. In a related embodiment, the antiinflammatory agent is selected from the group consisting of prednisone, methylprednisolone, paramethazone, 11-fludrocortisol, triamcinolone, betamethasone, dexamethasone, and beclomethasone.

In another preferred embodiment, the preparation method is used to produce a liposomal preparation for inflammation associated with psoriasis, and the liposome-entrapped antiinflammatory agent is selected from the group consisting of steroidal anti-inflammatory agents, non-steroidal antiinflammatory agents, methotrexate, azaribine, etretinate, anthralin, psoralins, and immunosuppressants such as cyclosporine.

DETAILED DESCRIPTION OF THE INVENTION

I. Preparation of Derivatized Lipids

Figure 1:
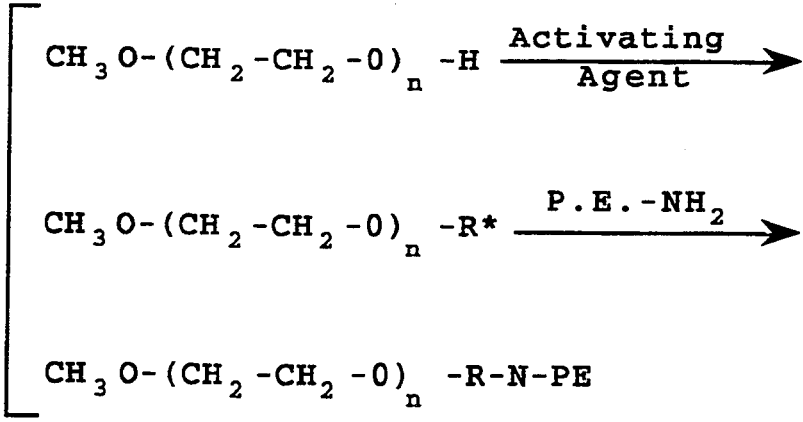
FIG. 1 illustrates a general reaction scheme for derivatizing a vesicle-forming lipid amine with a polyalkylether.

FIG. 1 shows a general reaction scheme for preparing a vesicle-forming lipid derivatized with a biocompatible, hydrophilic polymer, as exemplified by polyethylene glycol (PEG), polylactic acid (PLA), polyglycolic acid (PGA) and polyvinyl alcohol (PVA). These polymers are readily water soluble, can be coupled to vesicle-forming lipids, and are tolerated in vivo without toxic effects. The hydrophilic polymer which is employed, e.g., PEG, is preferably capped by a methoxy, ethoxy or other unreactive group at one end or, alternatively, has a chemical group that is more highly reactive at one end than the other. The polymer is activated at one of its ends by reaction with a suitable activating agent, designated R* in the figure, such as cyanuric acid, diimidazole, anhydride reagent, or the like, as described below. The activated compound is then reacted with a vesicle-forming lipid, such as a diacyl glycerol, including diacyl phosphoglycerols, where the two hydrocarbon chains are typically between 14–22 carbon atoms in length and have varying degrees of saturation, to produce the derivatized lipid. Phosphatidylethanolamine (PE) is an example of a phospholipid which is preferred for this purpose since it contains a reactive amino group which is convenient for coupling to the activated polymers. Alternatively, the lipid group may be activated for reaction with the polymer, or the two groups may be joined in a concerted coupling reaction, according to known coupling methods. PEG capped at one end with a methoxy or ethoxy group can be obtained commercially in a variety of polymer sizes, e.g., 500–20,000 dalton molecular weights.

The vesicle-forming lipid is preferably one having two hydrocarbon chains, typically acyl chains, and a polar head group. Included in this class are the phospholipids, such as phosphatidylcholine (PC), PE, phosphatidic acid (PA), phosphatidylinositol (PI), and sphingomyelin (SM), where the two hydrocarbon chains are typically between about 14–22 carbon atoms in length, and have varying degrees of unsaturation. Also included in this class are the glycolipids, such as cerebrosides and gangliosides.

Another vesicle-forming lipid which may be employed is cholesterol and related sterols. In general, cholesterol may be less tightly anchored to a lipid bilayer membrane, particularly when derivatized with a high molecular weight polymers, such as polyalkylether, and therefore be less effective in promoting liposome evasion of the RES in the bloodstream.

More generally, and as defined herein, "vesicle-forming lipid" is intended to include any amphipathic lipid having hydrophobic and polar head group moieties, and which (a) by itself can form spontaneously into bilayer vesicles in water, as exemplified by phospholipids, or (b) is stably incorporated into lipid bilayers in combination with bilayer forming phospholipids, with its hydrophobic moiety in contact with the interior, hydrophobic region of the bilayer membrane, and its polar head group moiety oriented toward the exterior, polar surface of the membrane. An example of a latter type of vesicle-forming lipid is cholesterol and cholesterol derivatives, such as cholesterol sulfate and cholesterol hemisuccinate.

According to one important feature of the invention, the vesicle-forming lipid may be a relatively fluid lipid, typically meaning that the lipid phase has a relatively low liquid to liquid-crystalline melting temperature, e.g., at or below room temperature, or relatively rigid lipid, meaning that the lipid has a relatively high melting temperature, e.g., up to 60° C. As a rule, the more rigid, i.e., saturated, lipids contribute to greater membrane rigidity in a lipid bilayer structure and also contribute to greater bilayer stability in serum. Other lipid components, such as cholesterol, are also known to contribute to membrane rigidity and stability in lipid bilayer structures. As mentioned above, a long chain (e.g. C-18) saturated lipid plus cholesterol is one preferred composition for delivering therapeutics to inflamed sites, since these liposomes do not tend to release the drugs into the plasma as they circulate through the bloodstream and enter the inflamed region during the first 48 hours following injection. Phospholipids whose acyl chains have a variety of degrees of saturation can be obtained commercially, or prepared according to published methods.

According to another important feature of the invention, the vesicle-forming lipid includes an amphipathic vesicle-forming lipid having a derivatized hydrophilic biocompatible polymer. In experiments in support of the invention, and as noted below, it has been found that the presence of such polymers derivatized to vesicle-forming lipids in liposomal compositions is effective to significantly enhance liposome blood circulation time, in comparison to liposomes formed from lipids in the absence of such derivatized hydrophilic polymers.

It will be appreciated that the polymer-derivatized lipids must be (a) safe for parenteral administration, both in terms of toxicity, biodegradability, and tissue compatibility, (b) compatible with stable lipid bilayer formation and structure, and (c) amenable to liposome preparation and processing steps. These requirements are met by PEG polymers which have been approved for human use in the U.S., and also by the thermoplastic polyester polymers polylactic acid and polyglycolic acid (also referred to as polylactide and polyglycolide), copolymers of lactide and glycolide, such as poly(lactide-co-glycolide), and polyvinyl alcohols. In particular, the polyester polymers are safe to administer because they biodegrade by undergoing random, nonenzymatic, hydrolytic cleavage of their ester linkages to form lactic acid and glycolic acid, which are normal metabolic compounds (Engelberg).

Figure 2:
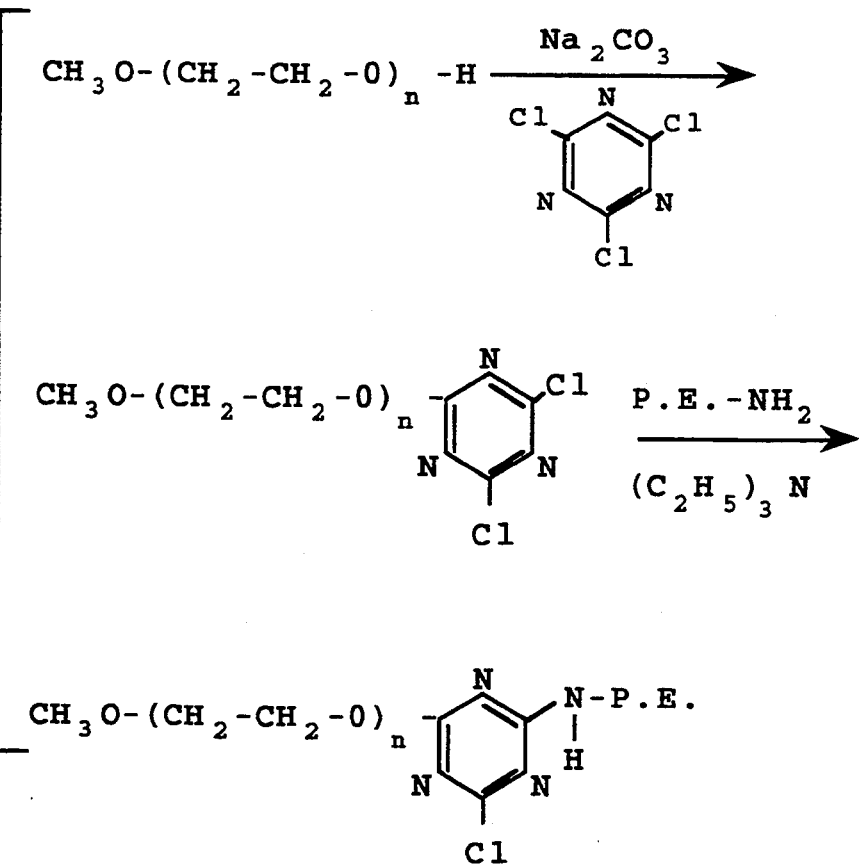
FIG. 2 is a reaction scheme for preparing phosphatidylethanolamine (PE) derivatized with polyethyleneglycol via a cyanuric chloride linking agent.

FIG. 2 shows a reaction scheme for producing a PE-PEG lipid in which the PEG is derivatized to PE through a cyanuric chloride group. Details of the reaction are provided in Example 1. Briefly, methoxy-capped PEG is activated with cyanuric chloride in the presence in sodium carbonate under conditions which produced the activated PEG compound shown in the figure. This material is purified to remove unreacted cyanuric acid. The activated PEG compound is reacted with PE in the presence of triethyl amine (TEA) to produce the desired PE-PEG compound shown in the figure. The yield is about 8-10% with respect to initial quantities of PEG.

The method just described may be applied to a variety of lipid amines, including PE, cholesteryl amine, and glycolipids with sugar-amine groups.

Figure 3:
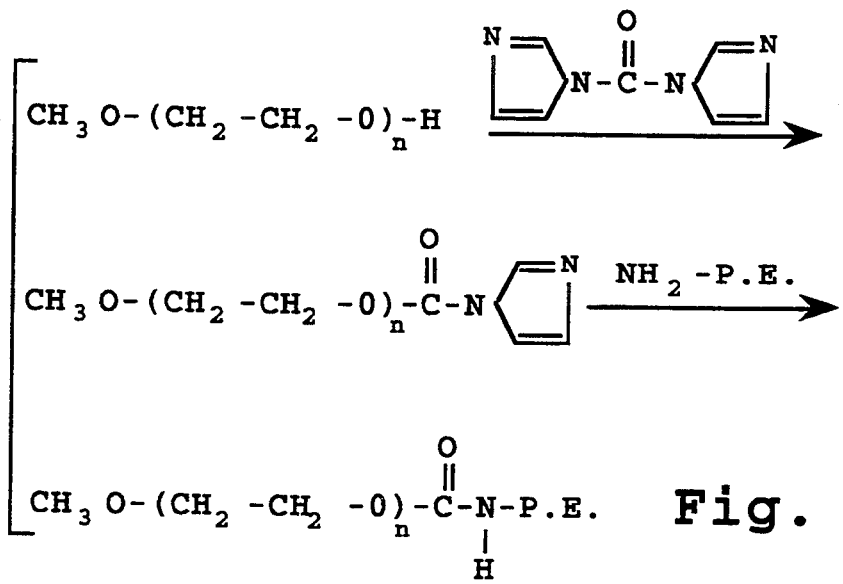
FIG. 3 illustrates a reaction scheme for preparing phosphatidylethanolamine (PE) derivatized with polyethyleneglycol by means of a diimidazole activating reagent.

A second method of coupling a polyalkylether, such as capped PEG to a lipid amine is illustrated in FIG. 3. Here the capped PEG is activated with a carbonyl diimidazole (CDI) coupling reagent, to form the activated imidazole compound shown in FIG. 3. Reaction with a lipid amine, such as PE leads to PEG coupling to the lipid through an amide linkage, as illustrated in the PEG-PE compound shown in the figure. Details of the reaction are given in Example 2.

Figure 4:
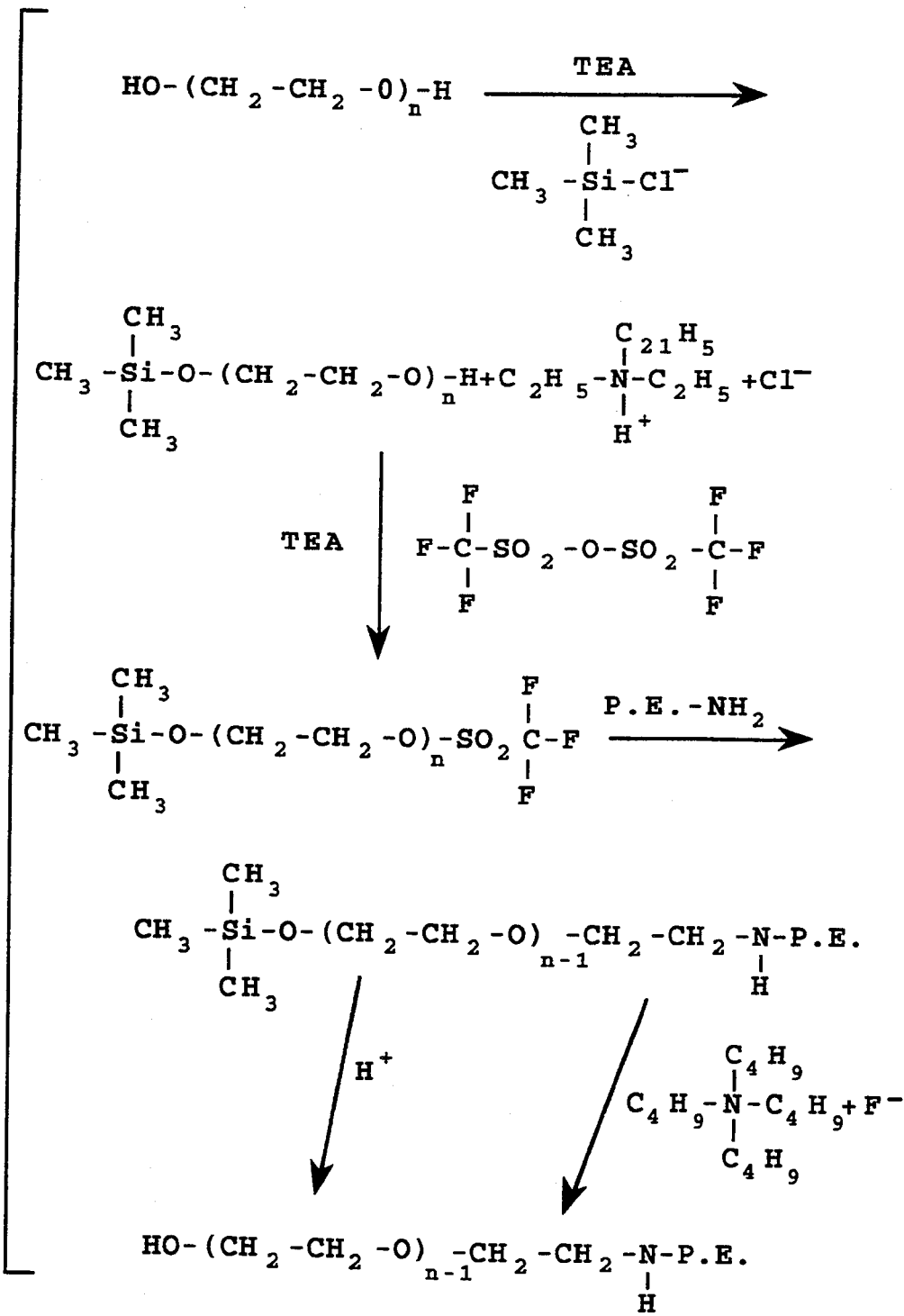
FIG. 4 illustrates a reaction scheme for preparing phosphatidylethanolamine (PE) derivatized with polyethyleneglycol by means of a trifluoromethane sulfonate reagent.

A third reaction method for coupling a capped polyalkylether to a lipid amine is shown in FIG. 4. Here PEG is first protected at its OH end by a trimethylsilane group. The end-protection reaction is shown in the figure, and involves the reaction of trimethylsilylchloride with PEG in the presence of triethylamine (TEA). The protected PEG is then reacted with the anhydride of trifluoromethyl sulfonate to form the PEG compound activated with trifluoromethyl sulfonate. Reaction of the activated compound with a lipid amine, such as PE, in the presence of triethylamine, gives the desired derivatized lipid product, such as the PEG-PE compound, in which the lipid amine group is coupled to the polyether through the terminal methylene carbon in the polyether polymer. The trimethylsilyl protective group can be released by acid treatment, as indicated in the figure, or, alternatively, by reaction with a quaternary amine fluoride salt, such as the fluoride salt of tetrabutylamine.

It will be appreciated that a variety of known coupling reactions, in addition to those just described, are suitable for preparing vesicle-forming lipids derivatized with hydrophilic polymers such as PEG, polylactic acid, polyglycolic acid, polylactic-polyglycolic copolymers and polyvinyl alcohol. For example, the sulfonate anhydride coupling reagent illustrated in FIG. 4 can be used to join an activated polyalkylether to the hydroxyl group of an amphipathic lipid, such as the 5'-OH of cholesterol. Other reactive lipid groups, such as an acid or ester lipid group may also be used for coupling, according to known coupling methods. For example, the acid group of phosphatidic acid can be activated to form an active lipid anhydride, by reaction with a suitable anhydride, such as acetic anhydride, and the reactive lipid can then be joined to a protected polyalkylamine by reaction in the presence of an isothiocyanate reagent.

Figure 5A:
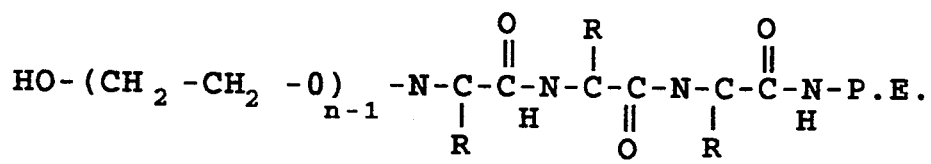
FIG. 5A through 5C illustrates a vesicle-forming lipid derivatized with polyethyleneglycol through a peptide (5A), ester (5B), and disulfide (5C) linkage.
Figure 5B:
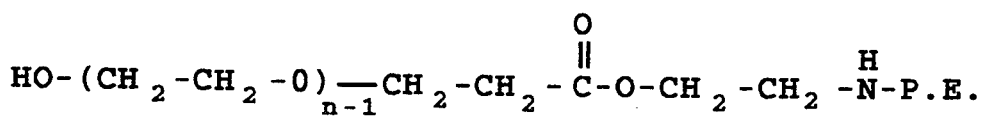
Figure 5C:
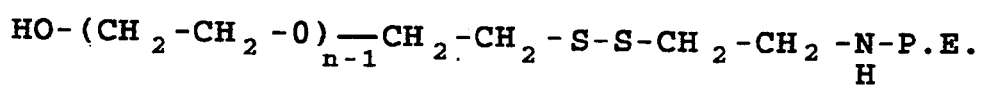

In another embodiment, the derivatized lipid components are prepared to include a labile lipid-polymer linkage, such as a peptide, ester, or disulfide linkage, which can be cleaved under selective physiological conditions, such as in the presence of peptidase or esterase enzymes or reducing agents such as glutathione present in the bloodstream. FIG. 5 shows exemplary lipids which are linked through (5A) peptide, (5B), ester, and (5C), disulfide containing linkages. The peptide-linked compound can be prepared, for example, by first coupling a polyalkylether with the N-terminal amine of the tripeptide shown, e.g., via the reaction shown in FIG. 3. The peptide carboxyl group can then be coupled to a lipid amine group through a carbodiimide coupling reagent conventionally. The ester linked compound can be prepared, for example, by coupling a lipid acid, such as phosphatidic acid, to the terminal alcohol group of a polyalkylether, using alcohol via an anhydride coupling agent. Alternatively, a short linkage fragment containing an internal ester bond and suitable end groups, such as primary amine groups can be used to couple the polyalkylether to the amphipathic lipid through amide or carbamate linkages. Similarly, the linkage fragment may contain an internal disulfide linkage, for use in forming the compound shown in FIG. 5C. Polymers coupled to phospholipids via such reversible linkages are useful to provide high blood levels of liposomes which contain them for the first few hours post injection. After this period, plasma components cleave the reversible bonds releasing the polymers and the "unprotected" liposomes are rapidly taken up by the RES by the same mechanism as conventional liposomes.

Figure 6:
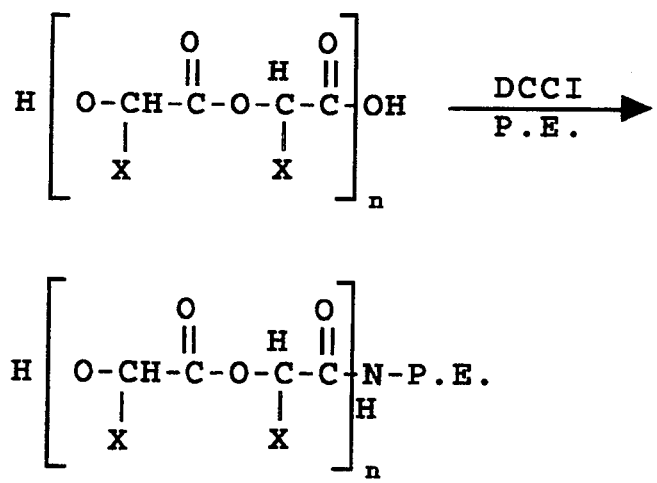
FIG. 6 illustrates a reaction scheme for preparing phosphatidylethanolamine (PE) derivatized with polylactic acid (PLA), polyglycolic acid (PGA), and copolymers of the two.

FIG. 6 illustrates a method for derivatizing polylactic acid, polyglycolic acid and polylactic-polyglycolic acid copolymers with PE in an amide linkage. The polylactic acid is reacted, in the presence of PE, with dicyclohexylcarbomide (DCCI), as detailed in Example 2. Similarly, a vesicle-forming lipid derivatized with polyglycolic acid may be formed by reaction of polyglycolic acid or glycolic acid with PE in the presence of a suitable coupling agent, such as DCCI, also as detailed in Example 2. Similar chemistry may be used to form lipid derivatives of polylactic-polyglycolic acid copolymers. Polyvinyl alcohol (PVA) is similarly derivatized with PE to form a carbamate linkage, as detailed in Example 2, by first reaching PE with carbonyl diimidazole (CDI), followed by addition of a low molecular weight fraction of PVA in the presence of triethylamine. The vesicle-forming lipids derivatized with either polylactic acid or polyglycolic acid and their copolymers or polyvinyl alcohol form part of the invention herein. Also forming part of the invention are liposomes containing these derivatized lipids.

II. Preparation of Liposomes

A. Lipid Components

The lipid components used in forming the liposomes of the invention may be selected from a variety of vesicle-forming lipids, typically including phospholipids, sphingolipids and sterols. As will be seen, one requirement of the liposomes of the present invention is long blood circulation lifetime. It is therefore useful to establish a standardized measure of blood lifetime which can be used for evaluating the effect of lipid components on blood halflife.

One method used for evaluating liposome circulation time in vivo measures the distribution of IV injected liposomes in the bloodstream and the primary organs of the RES at selected times after injection. In the standardized model which is used herein, RES uptake is measured by the ratio of total liposomes in the bloodstream to total liposomes in the liver and spleen, the principal organs of the RES. It should be noted that although uptake in such tissues is specifically into RES cells, the fixed macrophages of the liver and spleen, evaluation of RES uptake is conventionally carried out by measuring total uptake by the whole tissues. Thus, when stated herein that RES uptake was measured in the liver and spleen, it is understood that such uptake was primarily by the fixed macrophages of the liver and spleen. In practice, age and sex matched rats or mice are injected IV through the tail vein with a radiolabeled liposome composition, and each time point is determined by measuring total blood and combined liver and spleen radiolabel counts, as detailed in Example 5.

Since the liver and spleen, and specifically, the fixed macrophages in the liver and spleen, account for nearly 100% of the initial uptake of liposomes by the RES, the blood/RES ratio just described provides a good approximation of the extent of uptake from the blood to the RES in vivo. For example, a ratio of about 1 or greater indicates a predominance of injected liposomes remaining in the bloodstream, and a ratio below about 1, a predominance of liposomes in the RES. For most of the lipid compositions of interest, blood/RES ratios were calculated at 1, 2, 3, 4, and 24 hours post injection.

The liposomes of the present invention include a vesicle-forming lipid derivatized with a hydrophilic polymer, described in Section I. According to one aspect of the invention, it has been discovered that blood circulation half-lives in these liposomes are largely independent of the degree of saturation of the phospholipid components making up the liposomes. That is, the phospholipid components may be composed predominantly of fluidic, relatively unsaturated, acyl chains, or of more saturated, rigidifying acyl chain components. This feature of the invention is seen in Example 6, which examines blood/RES ratios in liposomes formed with PEG-PE, cholesterol, and PC having varying degrees of saturation (Table 4). As seen from the data in Table 5 in the example, high blood/RES ratios were achieved in substantially all of the liposome formulations, independent of the extent of lipid unsaturation in the bulk PC phospholipid, and no systematic trend, as a function of degree of lipid saturation, was observed.

Accordingly, the vesicle-forming lipids may be selected to achieve a selected degree of fluidity or rigidity, to control the stability of the liposomes in serum and the rate of release of entrapped drug from the liposomes in the bloodstream and/or inflamed region. The vesicle-forming lipids may also be selected, in lipid saturation characteristics, to achieve desired liposome preparation properties. It is generally the case, for example, that more fluidic lipids are easier to formulate and down-size by extrusion and homogenization methods than more rigid lipid compositions.

Figure 9:
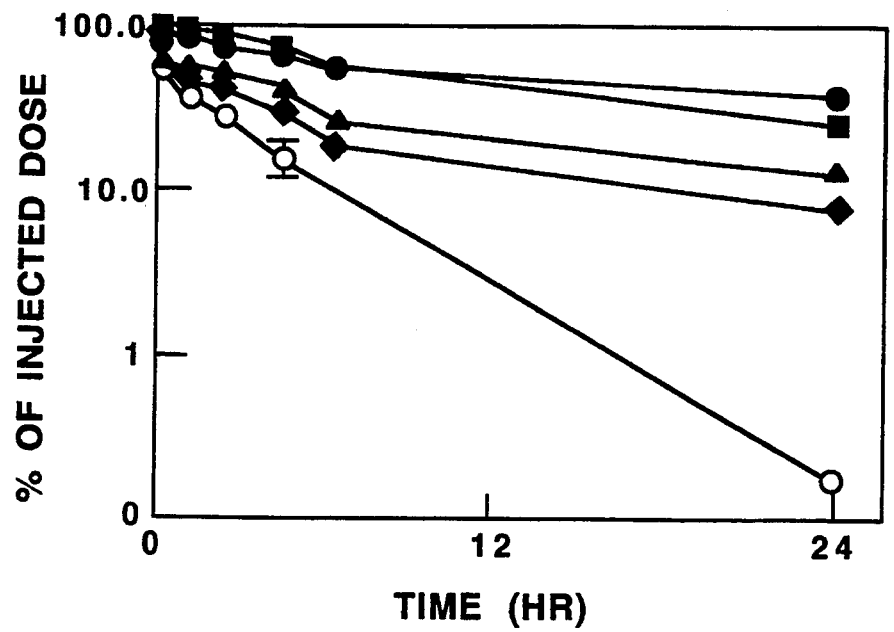
FIG. 9 is a plot similar to that of FIG. 7, showing the blood residence times of liposomes formulated with less than 35 mole percent cholesterol and a hydrophilic polymer (PEG-1900)-derivatized PE (solid circles), 50 mole percent cholesterol and PEG-1900-PE (solid squares), with PEG having a molecular weight of 750 ($^{750}$PEG-PE; solid triangles), with PEG having a molecular weight of 350 ($^{350}$PEG-PE; solid diamonds) and in the absence of hydrophilic polymeric coating ("conventional"; open circles)

Similarly, it has been found that the percentage of cholesterol in the liposomes may be varied over a wide range without significant effect on observed blood/RES ratios. The studies presented in Example 7A, with reference to Table 6 therein, show virtually no change in blood/RES ratios in the range of cholesterol between 0–30 mole percent. On the other hand, cholesterol content may affect the kinetics of drug distribution from the liposomes. For example, delayed release of corticosteroids has been demonstrated in liposomal compositions having high (greater than 50 mole percent) steroidal components, including cholesterol and cholesterol sulfate, as described in co-owned, co-pending allowed patent application 07/444,360, filed Dec. 1, 1989, herein incorporated by reference. Example 7C describes experiments in which hydrophilic polymer (methoxy PEG-1900-DSPE)-containing liposomes were prepared using high cholesterol concentrations (50 mole percent). The blood/RES distribution of these liposomes was determined (solid circles) in comparison to PEG-containing liposomes having less than 35 mole % cholesterol (solid squares) and "conventional" liposomes lacking derivatized hydrophilic polymers (FIG. 9). It is apparent that the presence of a high mole percent of cholesterol is not detrimental to the ability of PEG-containing liposomes to prolong blood circulation time, and may actually enhance this effect.

It has also been found, in studies conducted in support of the invention, that blood/RES ratios are also relatively unaffected by the presence of charged lipid components, such as phosphatidylglycerol (PG). This can be seen from FIG. 7, which plots percent loss of encapsulated marker for PEG-PE liposomes containing either 4.7 mole percent PG (triangles) or 14 mole percent PG (circles). Virtually no difference in liposome retention in the bloodstream over a 24 hour period was observed. The option of including negative charge in the liposome without aggravating RES uptake provides a number of potential advantages. Liposome suspensions which contain negative charge tend to be less sensitive to aggregation in high ionic strength buffers and hence physical stability is enhanced. Also, negative charge present in the liposome membrane can be used as a formulation tool to effectively bind high amounts of cationic drugs.

The vesicle-forming lipid derivatized with a biocompatible hydrophilic polymer is also present in the liposomal composition. The amount of such derivatized hydrophilic polymer is preferably between about 1–20 mole percent, on the basis of moles of derivatized lipid as a percentage of total moles of vesicle-forming lipids. These preferred mole ratios are applicable particularly to lipids derivatized with PEG having molecular weights between about 1,000–5,000 daltons. It will be appreciated that a lower mole ratio, such as less than one mole percent, may be appropriate for a lipid derivative with a large molecular weight polymer, and that such a composition may be effective in achieving significantly enhanced liposome blood-circulation times when the hydrophilic polymer, e.g., PEG, has a relatively high molecular weight, e.g., greater than about 1,000–5,000 daltons. Conversely, a higher mole ratio will be effective for a lipid derivative having a low molecular weight polymer, such as PEG having a molecular weight of 350 daltons. Such a composition may also be effective in achieving significantly enhanced liposome blood-circulation times. This is illustrated in FIG. 9, which shows the blood-circulation time for liposomes composed of PEG having molecular weights of 750 ($^{750}$PEG-PE; solid triangles) and 350 ($^{350}$PEG-PE; solid diamonds) were used at 33% molar ratios in liposome compositions. As seen, both compositions exhibited extended blood circulation times characteristic of the present invention. Specifically, as illustrated in FIG. 9, such compositions extend blood circulation time as measured 24 hours after injection of the liposomes, at least severalfold over that achievable by liposomes lacking derivatized hydrophilic polymers ("conventional" liposomes, open circles).

As noted in Section I, the hydrophilic polymer in the derivatized lipid preferably has a molecular weight between about 200–20,000 daltons, and more preferably between about 300–5,000 daltons. Example 7B, which examines the effect of very short ethoxy ether moieties on blood/RES ratios indicates that polyether moieties of greater than about 5 carbon ethers are required to achieve significant enhancement of blood/RES ratios.

B. Preparing the Liposome Composition

The liposomes may be prepared by a variety of techniques, such as those detailed in Szoka et al, 1980. One method for preparing drug-containing liposomes is the reverse phase evaporation method described by Szoka et al. and in U.S. Pat. No. 4,235,871, which is incorporated herein by reference. The reverse phase evaporation vesicles (REVs) have typical average sizes between about 2–4 microns and are predominantly oligolamellar, that is, contain one or a few lipid bilayer shells. The method is detailed in Example 4A.

Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium, as detailed in Example 4B. The lipid film hydrates to form MLVs, typically with sizes between about 0.1 to 10 microns.

In accordance with one important aspect of the invention, the liposomes are prepared to have substantially homogeneous sizes in a selected size range between about 0.07 and 0.2 microns. In particular, it has been discovered that liposomes in this size range are readily able to extravasate into inflamed regions, as discussed in Section III below, and at the same time, are capable of carrying a substantial drug load to an inflamed region and are capable of being filter sterilized. Although small unilamellar vesicles of less than $0.07\mu$ can easily extravasate into inflamed regions, they are severely restricted in drug-loading capacity. The upper end of this preferred size range, 0.2 microns, is not necessarily the largest size liposome capable of extravasation, rather it is approximately the upper limit of size of liposome which can be conventionally filter sterilized prior to administration. It can be appreciated that, allowing for adjustments in pharmaceutical formulation procedures, liposomal compositions above or below this size range may be effective in delivering drugs to an inflamed region.

One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. This method of liposome sizing is used in preparing homogeneous-size reverse evaporation vesicle (REV) and multilamellar vesicle (MLV) compositions described in the examples below. A more recent method involves extrusion through an asymmetric ceramic filter. The method is detailed in U.S. Pat. No. 4,737,323 for Liposome Extrusion issued Apr. 12, 1988, incorporated herein by reference. Homogenization methods are also useful for down-sizing liposomes to sizes of 100 nm or less (Martin).

Other methods of reducing particle size include application of high pressures to the liposomes, as in a French Press, and homogenization of the liposomes. In experiments carried out in support of the present invention, high pressure extrusion was generally used to control particle size.

C. Compound Loading

Incorporation of compound into liposomes can be achieved by one or more of a variety of active and passive methods. These methods and characteristics of exemplary compounds for use with these methods are described in detail in co-owned U.S. patent application Ser. No. 642,321, filed Jan. 15, 1991, which is incorporated herein by reference.

Passive loading by entrapment is employed for certain markers, as described in Example 4, and for certain antiinflammatory agents, particularly those which are therapeutically active at relatively low drug doses, and/or which are highly soluble in aqueous solutions. Here the drug is either dissolved in the aqueous phase used to hydrate the lipid or included with the lipids in liposome formation process, depending on the solubility of the compound.

Where the antiinflammatory composition includes a peptide or protein drug, the liposomes are preferably prepared by the reverse phase method, by a solvent injection system, such as described in U.S. Pat. No. 4,752,425, which is incorporated herein by reference, or by rehydrating a freeze dried mixture of the protein and a suspension of small unilamellar vesicles with water. Both methods combine passive loading with relatively high encapsulation efficiency, e.g., up to 50% efficiency. Nonencapsulated material can be readily removed from the liposome suspension, e.g., by dialysis, diafiltration or exclusion chromatography.

One class of antiinflammatory agents useful in the invention described herein, the antiinflammatory corticosteroids, are characterized by a high degree of lipophilicity. Another useful antiinflammatory agent, cyclosporine, similarly is highly lipophilic. The concentration of hydrophobic drug which can be accommodated in the liposomes will depend on drug/lipid interactions in the membrane, but is generally limited to a drug concentration of less than about 20 $\mu$g drug/mg lipid. It has been found that for certain hydrophobic drugs, the highest concentration of encapsulated material which can be achieved by passive loading is limited by their low intrinsic water solubility. It has also been found that liposomal trapping and delivery of certain antiinflammatory steroids is enhanced by inclusion of a relatively high concentration (greater than 50 mole percent) of cholesterol in the liposome composition, as described in co-pending, co-owned, and allowed U.S. patent application Ser. No. 07/444,360, filed Dec. 1, 1989, now U.S. Pat. No. 5,192,528 and co-owned U.S. Pat. Nos. 5,049,389 and 5,043,165, all of which are incorporated herein by reference.

Example 12 describes a method of preparing a steroidal liposomal composition. In this procedure, a mixture of liposome-forming components along with the selected corticosteroid drug, are dissolved in a suitable solvent, and the lipid solution is evaporated in a vessel to form a thin film, which is then covered by an aqueous medium. With addition of a suitable aqueous medium, such as phosphate buffered saline medium, the lipid film hydrates to form MLVs, typically with sizes between about 0.1 to 10 microns. Aqueous medium is preferably added to a final lipid concentration of between about 10–100 $\mu$mole-ml, and preferably about 40 $\mu$mole/ml. Liposomes are then sized by extrusion, as described in Example 4.

In the case of amphipathic drugs having a positive charge, it has been found that inclusion of 20–30 mole percent of an anionic phospholipid such as PG is in the liposomal membrane results in increasing the loading factor significantly through formation of an "ion pair" complex with the negatively charged PG at the membrane interface. However, such charged complexed formulations may have limited utility in the context of the present invention because the drugs tend to be rapidly released from the liposome membrane when introduced into plasma.

In some cases, in order to entrap high concentrations of drugs in liposomes, it has been found to be useful to use active loading methods. One method for active loading of amphipathic drugs into liposomes is described in co-owned U.S. patent application Ser. No. 413,037, filed Sep. 28, 1988, now U.S. Pat. No. 5,192,549 and incorporated herein by reference. In this method, liposomes are prepared in the presence of a relatively high concentration of ammonium ion sulfate. After sizing the liposomes to a desired size, the liposome suspension is treated to create an inside-to-outside ammonium ion gradient across the liposomal membranes. The gradient may be created by dialysis or diafiltration against a non-ammonium containing medium, such as an isotonic glucose medium, or by gel filtration, such as on a Sephadex G-50 column equilibrated with 0.15M NaCl or KCl effectively replacing ammonium sulfate in the exterior phase with sodium or potassium ions or a non-electrolyte species. Alternatively, the liposome suspension may be diluted with a non-ammonium solution, thereby reducing the exterior-phase concentration of ammonium ions. The ammonium sulfate concentration inside the liposomes is preferably at least 10 times, and more preferably at least 100 to 1000 times that in the external liposome phase.

The ammonium sulfate gradient across the liposomes in turn creates a chemical gradient which permits capturing of unionized amines as they pass through the membrane, as ammonia is released across the liposome membrane, and the drugs are protonated and trapped in the internal aqueous phase of the liposome. To load liposomes with the selected drug a suspension of the liposomes, e.g., about 20-200 mg/ml lipid, is mixed with an aqueous solution of the drug, and the mixture is allowed to equilibrate over a period of time, e.g., several hours, at temperatures ranging from room temperature to 60° C.—depending on the phase transition temperature of the lipids used to form the liposome. In one typical method, a suspension of liposomes having a lipid concentration of 50 $\mu$moles/ml is mixed with an equal volume of amphipathic drug at a concentration of about 5-8 mg/ml. At the end of the incubation period, the suspension is treated to remove free (unbound) drug. One preferred method of drug removal for drugs is by passage over an ion exchange resin, such as Dowex 50 WX-4, which is capable of binding unencapsulated drug, but not liposomes containing the drug.

After liposome formation, loading and sizing, free (unbound) drug is usually removed by ion exchange or gel exclusion chromatographic methods known in the art or by dialysis or diafiltration. Ion exchange resins are selected for use, according to the chemical properties, and particularly the charge, of the free drug in solution. An example of an ion exchange resin which is generally useful in removal of unbound cationic drugs is Dowex AG50W. Such a resin can be used in a batch or a column mode, using standard methods known in the art. In order to complete removal of free drug using a batch method, two treatments with the ion exchange resin may be required. An example a gel exclusion chromatography column used for removal of free drug is a Sephadex G-50 sizing column. Following drug removal using this method, concentration of liposomes can be achieved by one or more techniques standard to concentration of macromolecules. One particularly useful technique includes repeated centrifugation in a Centriprep 10 centrifuge concentrator (Aminco, Danvers, Mass.) following manufacturers instructions.

D. Characterization of Drug-entrapped Liposomal Compositions

Liposomal drug formulations are characterized by measurements of particle size, lipid concentration, and pH by standard methods as described above. Drug incorporation into the composition can be determined by inclusion of radiolabeled tracer, such as $^{125}$I-labeled drug tracer, into test compositions. The amount of liposome-entrapped drug is then determined by gel permeation chromatography using BioRad A-15M resin. Liposomal drug fraction is calculated from the amount of radiolabel present in the void volume of the column. The percentage of liposomal drug is then determined from the ratio of the label eluting in the void volume to the remaining label eluting from the column.

III. Liposome Localization in Inflamed Regions

A. Extended Bloodstream Halflife

One of the requirements for liposome localization in a target inflamed tissue, in accordance with the invention, is an extended liposome lifetime in the bloodstream following parenteral liposome administration. One measure of liposome lifetime in the bloodstream is the blood/RES ratio determined at a selected time after liposome administration, as discussed above. Blood/RES ratios for a variety of liposome compositions are given in Table 3 of Example 5. In the absence of PEG-derivatized lipids, blood/RES ratios were 0.03 or less. In the presence of PEG-derivatized lipids, the blood/RES ratio ranged from 0.2, for low-molecular weight PEG, to between 1.7-4 for several of the formulations, one of which lacks cholesterol, and three of which lack an added charged phospholipid (e.g., PG).

The data presented in Table 5 in Example 6 show blood/RES ratios (excluding two points with low percent recovery) between about 1.26 and 3.27, consistent with the data given in Table 3. As noted in Section II above, the blood lifetime values are substantially independent of degree of saturation of the liposome lipids, presence of cholesterol and presence of charged lipids.

The blood/RES values reported above can be compared with blood/RES values reported in co-owned U.S. Pat. No. 4,920,016, which used blood/RES measurement methods similar to those used in generating the data presented in Tables 3 and 5. The best 24-hour blood/RES ratios which were reported in the above-noted patent was 0.9, for a formulation composed of $GM_1$, saturated PC, and cholesterol. The next best formulations gave 24-hour blood/RES values of about 0.5. Thus, typical 24-hour blood/RES ratios obtained in a number of the current formulations were more than twice as high as the best formulations which have been reported using liposomes lacking derivatized hydrophilic polymers. Further, ability to achieve high blood/RES with $GM_1$ or HPI lipids was dependent on the presence of predominantly saturated lipids and cholesterol in the liposomes.

Figure 7:
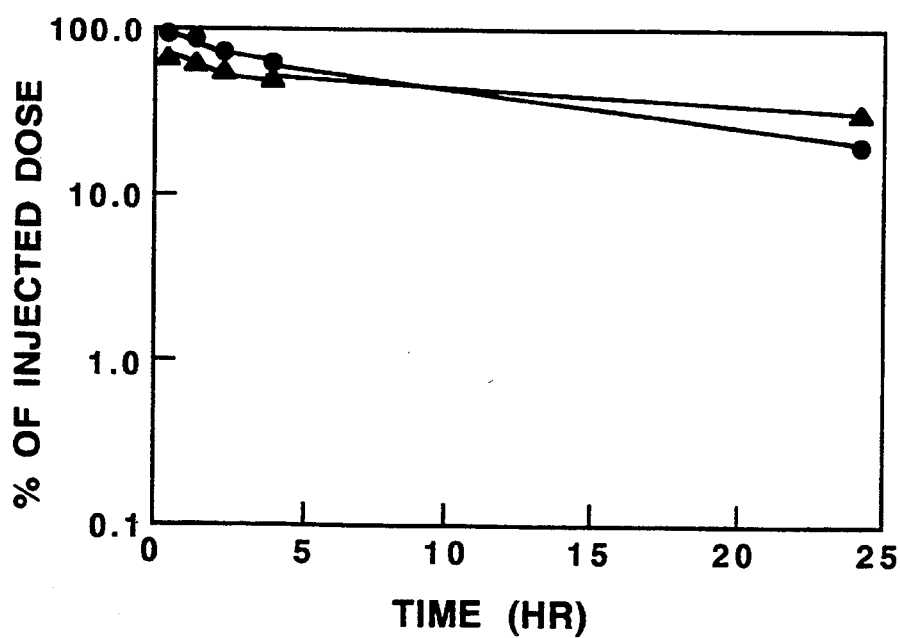
FIG. 7 is a plot of liposome residence times in the blood, expressed in terms of percent injected dose as a function of hours after IV injection, for PEG-PE liposomes containing 4.7 (triangles) or 14 (circles) mole percent of phosphatidylglycerol.
Figure 8A:
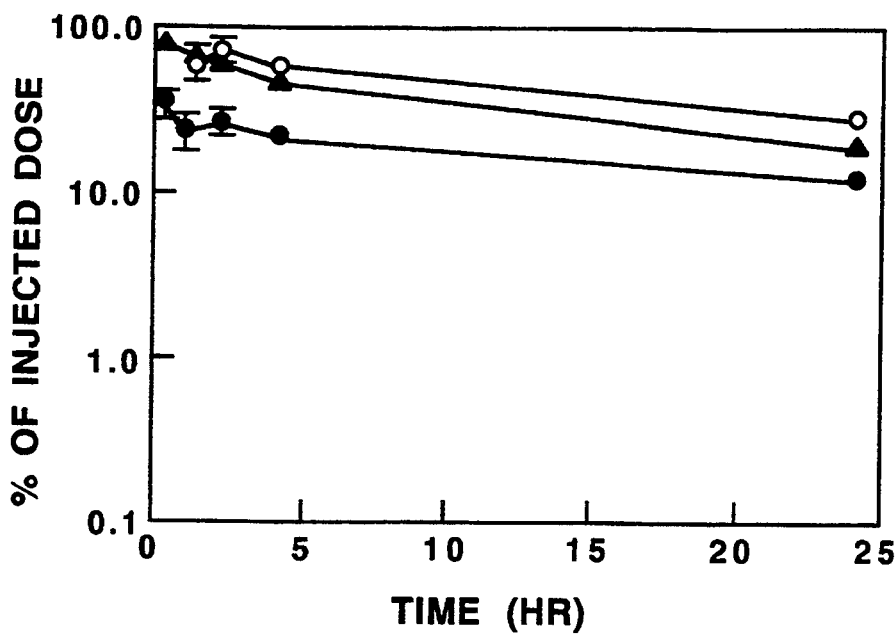
FIG. 8A is a plot similar to that of FIG. 7, showing blood residence times of liposomes composed of predominantly unsaturated phospholipid components.

Plasma pharmacokinetics of a liposomal marker in the bloodstream can provide another measure of the enhanced liposome lifetime which is achieved by the liposome formulations of the present invention. FIGS. 7 and 8A discussed above show the slow loss of liposomal marker from the bloodstream over a 24 hour period in typical PEG-liposome formulations, substantially independent of whether the marker is a lipid or an encapsulated water-soluble compound (FIG. 8A). In both plots, the amount of liposomal marker present 24 hours after liposome injection is greater than 10% of the originally injected material.

Figure 8B:
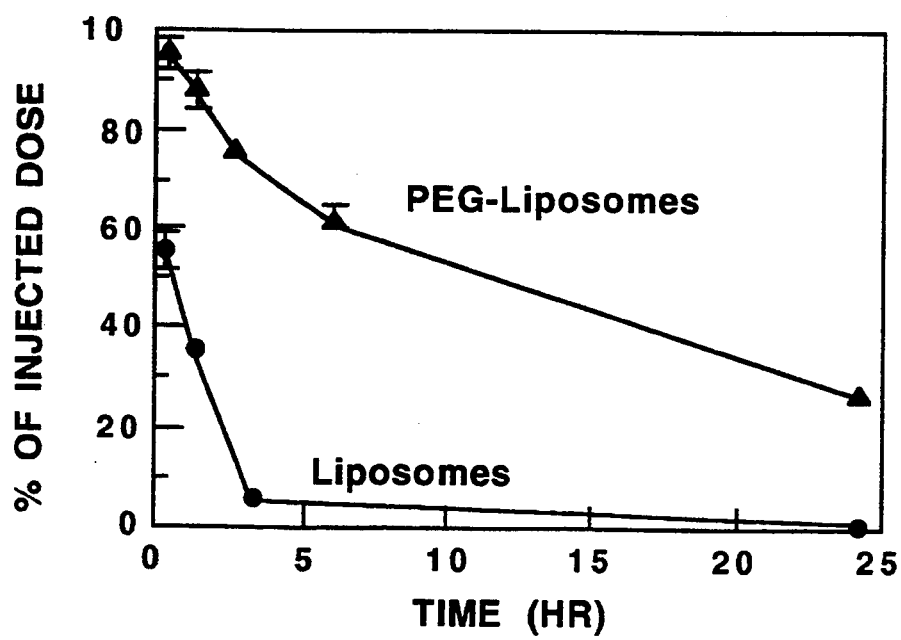
FIG. 8B is a plot similar to that of FIG. 7, showing the blood residence times of PEG-coated liposomes (solid triangles) and conventional, uncoated liposomes (solid circles)

FIG. 8B shows the kinetics of liposome loss from the bloodstream for a typical PEG-liposome formulation and the same liposomes in the absence of a PEG-derivatized lipid. After 24 hours, the percentage of PEG-liposomes remaining in the blood was greater than about 20%, whereas the conventional liposomes showed less than 5% retention in the blood after 3 hours, and virtually no detectable marker at 24 hours. FIG. 9 shows the kinetics of liposome loss from the bloodstream for low molecular weight PEG liposome formulations using DSPE derivatized to PEG having a molecular weight of 350 (350 PEG, open triangles) or 750 (750 PEG, closed triangles). These formulations showed blood retention times similar to those observed with liposomes formulated using higher molecular weight PEG (typically 1000-5000 daltons).

Similarly, liposomes containing PLA- or PGA-derivatized PE or PVA-derivatized DSPE show plasma kinetics which are superior to conventional liposomes consisting of PG, PC and cholesterol (FIGS. 10 and 11), in that the liposomes containing the derivatized PE or DSPE are cleared from the bloodstream at a rate which is severalfold slower than the formulations without the derivatized PE or DSPE.

The results seen in FIGS. 7-11 are consistent with 24 hour blood liposome values measured for a variety of liposome formulations, and reported in Tables 3 and 5-7 in Example 5-8 below. As seen in Table 3 in Example 5, the percent dose remaining at 24 hours was less than 1% for conventional liposomes, versus at least 5% for the PEG-liposomes. In the best formulations, values between about 20-40% were obtained. Similarly in Table 5 from Example 6, liposome levels in the blood after 24 hours (again neglecting two entries with low recovery values) were between 12 and about 25 percent of total dose given. Similar results are reported in Tables 6 and 7 of Example 7.

For both blood/RES ratios, and liposome retention time in the bloodstream, the data obtained from a model animal system can be reasonably extrapolated to humans and veterinary animals of interest. This is because uptake of liposomes by the fixed macrophages of liver and spleen has been found to occur at similar rates in several mammalian species, including mouse, rat, monkey, and human (Gregoriadis, 1974; Jonah; Kimelberg, 1976; Juliano; Richardson; Lopez-Berestein). This result likely reflects the fact that the biochemical factors which appear to be most important in liposome uptake by the RES—including optimization by serum lipoproteins, size-dependent uptake effects, and cell shielding by surface moieties—are common features of all mammalian species which have been examined.

In studies carried out in support of the present invention, in a set of healthy control animals liposome accumulation in the liver and spleen were less than 20% and 10%, respectively, of the injected dose over a monitoring period of 40 hours. These levels are well below the levels maintained in the blood during most of the monitoring period, and significantly, during the first 24 hours following injection.

Comparison of PEG-containing liposomes of the invention with conventional liposome preparations reveals that a desirable feature of anti-inflammatory therapy—prolongation of blood levels of drug-carrying liposomes for two or more days in order to give increased and sustained accumulation in target sites—was not achieved by conventional liposomal preparations, but is achieved with the hydrophilic polymer-derivatized liposomal formulation of the invention, as exemplified by PEG-, PGA-, PLA-, and PVA-derivatized liposomal formulations (FIGS. 8B, 9, 10 and 11).

B. Extravasation into Inflamed Tissues

Another required feature for high-activity liposome targeting to an inflamed region, in accordance with the invention, is liposome extravasation into the region from the bloodstream through the endothelial cell barrier and underlying basement membrane separating a capillary from the tissue cells supplied by the capillary. Liposomes with sizes between about 0.07 and 0.2 microns exhibit this ability to extravasate into inflamed regions. Although liposomes with sizes of less than 0.07 microns would also be expected to extravasate, a limited drug-carrying capacity of these small liposomes render them less effective as drug carriers for the present system. Similarly, liposomal sizes greater than 0.2 microns may also extravasate to inflamed regions; however, as stated in Section II, such liposomes cannot easily be filter sterilized, following hydration, in conventional pharmaceutical production. For the purposes of the present invention, then, the optimal size range for liposomes would strike a balance between ability to extravasate, drug-carrying capacity, and feasibility of sterile filtration, that is, between about 0.07 and 0.2 microns in diameter.

Figure 12A:
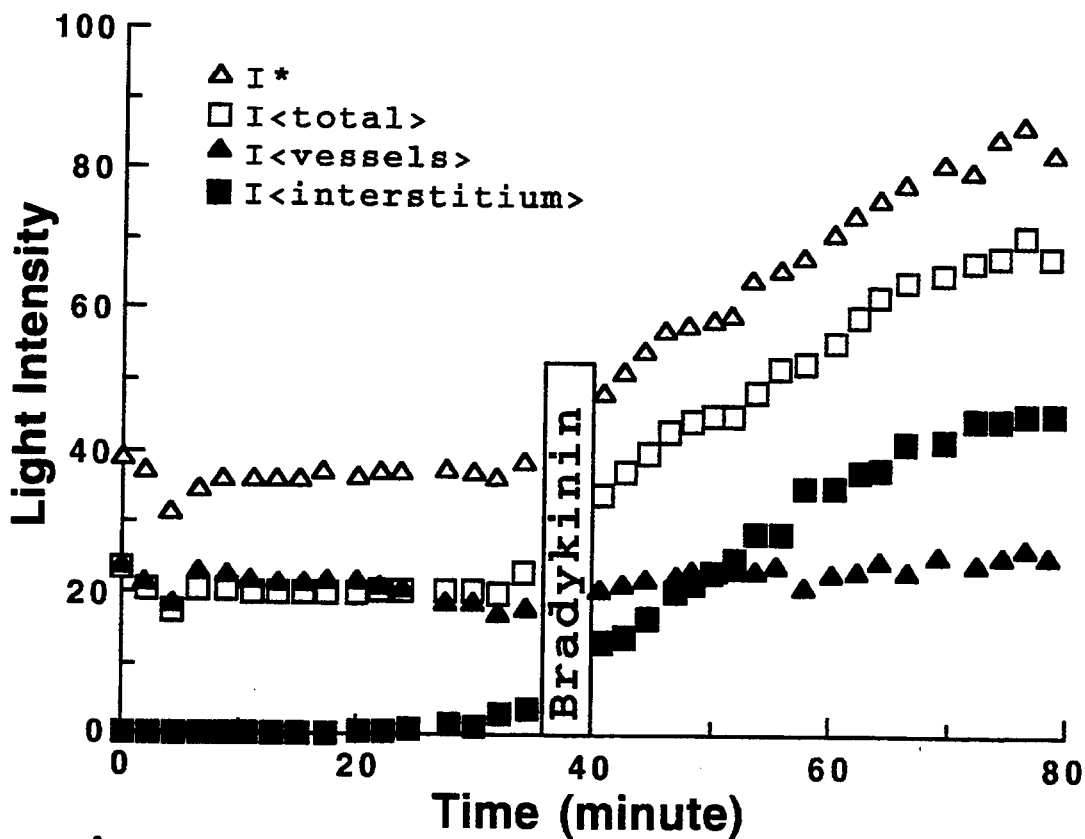
FIG. 12A shows a time course plot of light emission (intensity) from fluorescently labeled albumin in the specific regions within the blood vessels (as a reference) (I*, open triangles), entire tissue area (I<total>, open squares), total blood vessels (closed triangles), and total interstitium (closed squares) in a rat skin flap window model before and after application of bradykinin (Bradykinin, open bar), monitored by video-enhanced fluorescence microscopy.
Figure 13A:
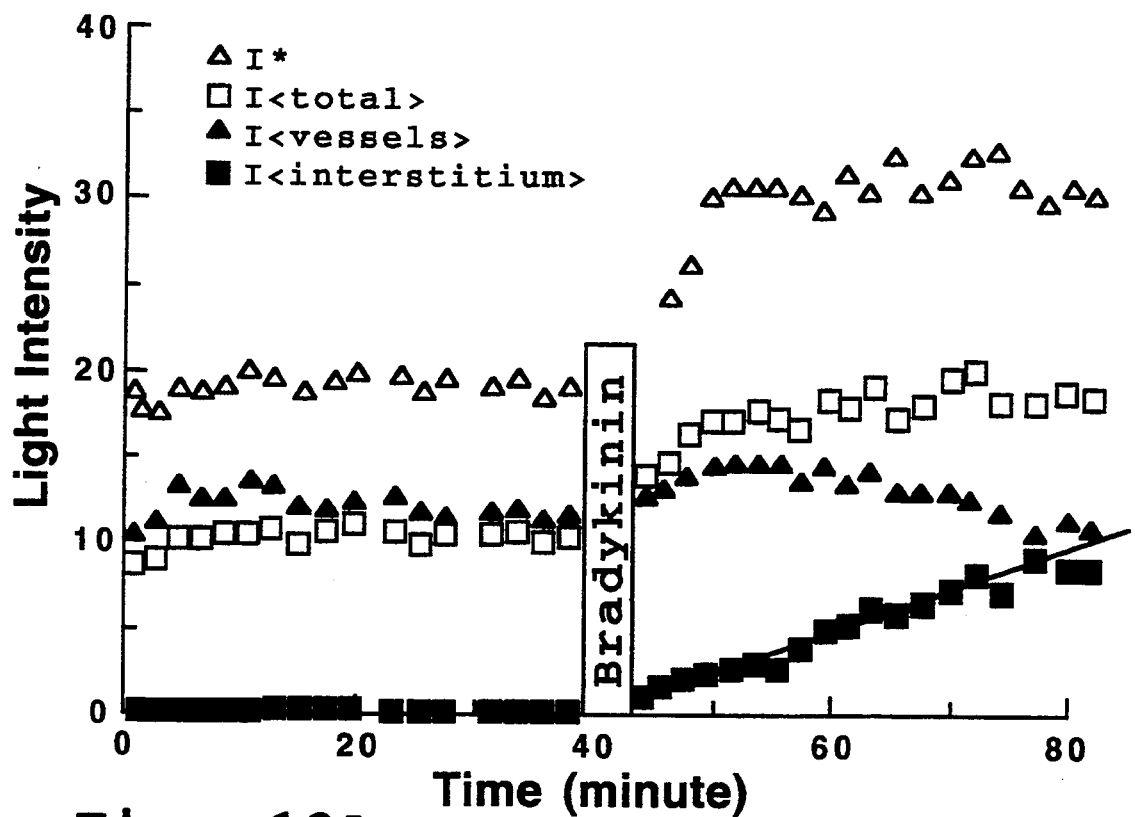
FIG. 13A shows a time course plot of light emission (intensity) from fluorescently labeled liposomes in the specific regions within the blood vessels (as a reference) (I*, open triangles), entire tissue area (I<total>, open squares), total blood vessels (closed triangles), and interstitium (closed squares) in a rat skin flap window model before and after application of bradykinin (Bradykinin, open bar)

In experiments carried out in support of the present invention, detailed in Example 10, fluorescently labeled PEG-containing and a fluorescently labeled protein (bovine serum albumin) were employed to examine extravasation characteristics in a model of bradykinin-induced inflammation. FIG. 12A and FIG. 13A show plots of the appearance of the fluorescently labeled bovine serum albumin (BSA; FIG. 12A) and liposomes (FIG. 13A) in the vascular (solid triangles) and interstitial regions (solid squares) before and after bradykinin application to the region. Sharp increases in fluorescence attributable to BSA-associated label and to liposome-associated label were observed in the interstitial region just after application of bradykinin, indicating extravasation to the interstitium. Visual assessment of the regions confirmed the accumulation of protein and liposomes in the interstitial region, by the presence of bright fluorescent spots following bradykinin treatment (FIGS. 14C and 14E). Such visually apparent fluorescence was not observed prior to the application of bradykinin to the region.

Figure 12B:
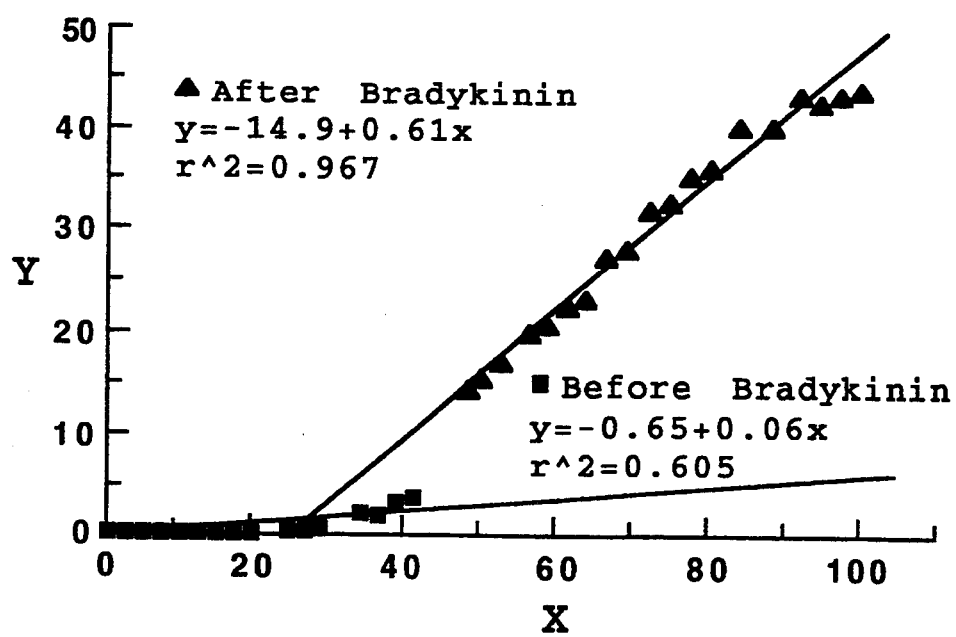
FIG. 12B shows the same data as in FIG. 12A plotted as fluorescence intensity (Y) vs. time (X) before (solid squares) and after (solid triangles) application of bradykinin.
Figure 13B:
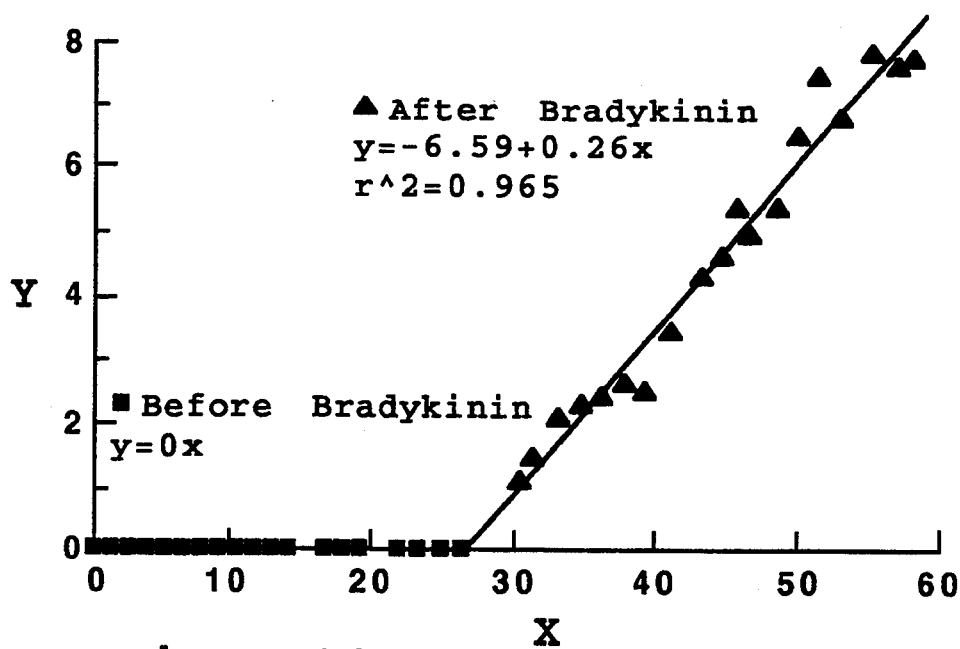
FIG. 13B shows the same data as in FIG. 13A plotted as fluorescence intensity (Y) vs. time (X) before (solid squares) and after (solid triangles) application of bradykinin.

These data were converted to a plot of averaged permeability constants (FIG. 12B and FIG. 13B), calculated according to the permeability equation (Wu, 1991) and shown as fluorescence intensity (Y) in the figures, as a function of time (X). As plotted, permeability is proportional to the slope, $\alpha$, of the plot of Y vs. X. Using these calculations, a 10-fold increase in vascular permeability to albumin was measured following bradykinin treatment. Prior to bradykinin application, permeability to liposomes was essentially zero, so that a fold-comparison cannot be made. However, permeability of 90 nm liposomes was about ⅓ that of albumin, just following bradykinin treatment, and about 4 times that of albumin measured subsequent to bradykinin treatment.

Figure 15:
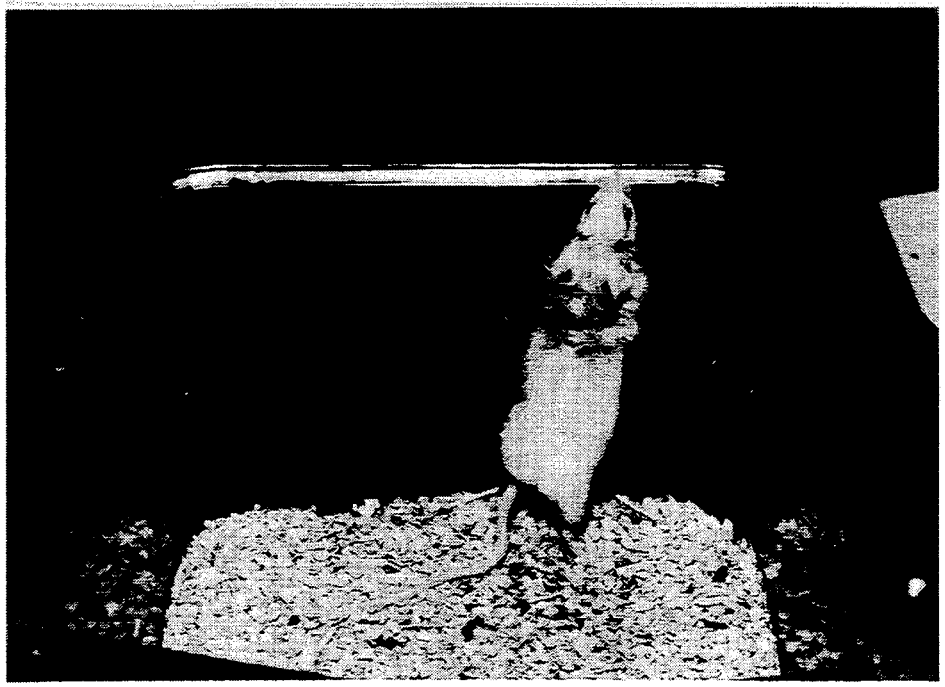
FIG. 15 shows a FSN mouse with psoriasis gene mutation exhibiting a psoriatic lesion characterized by a nude patch with erythematous and large parakeratotic crusts.
Figure 16A:
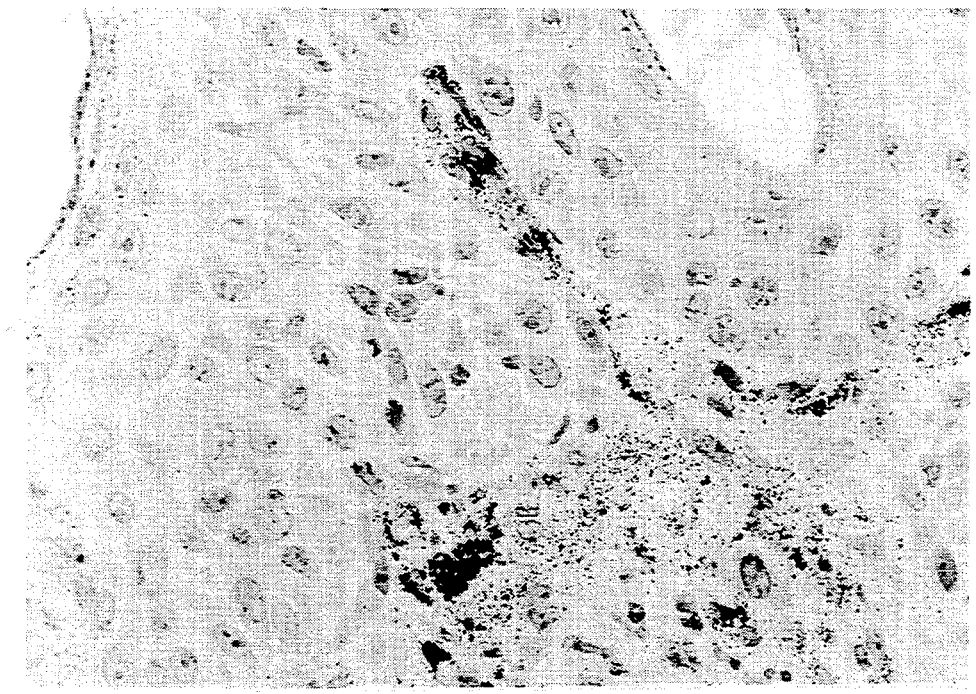
FIGS. 16A–16C show micrographs of tissue sections of a psoriatic lesion having liposomes concentrated therein.

In further experiments carried out in support of the present invention, concentration of liposomes in an area of inflammation in a mouse model of psoriasis was examined, as detailed in Example 11. Briefly, strain FSN mice having a single gene immunologic mutation which results in development of dermal lesions resembling human psoriasis (Sundberg, et al.), were used. A mouse with such a lesion is shown in FIG. 15. Erythematous and large parakeratotic crusts were characteristic of the psoriatic lesions. Histologic examination of the lesions revealed squirting papilla with focal paraketosis and proliferated mast cells in the region between dermis and epidermis, as shown in FIG. 16A. Colloidal gold-containing PEG-containing were injected into these mice. The mice were sacrificed 24 hours after liposome injection, tissues were collected following fixation, and tissue sections were prepared for silver enhancement of gold deposition, as detailed in Example 11.

Figure 16B:
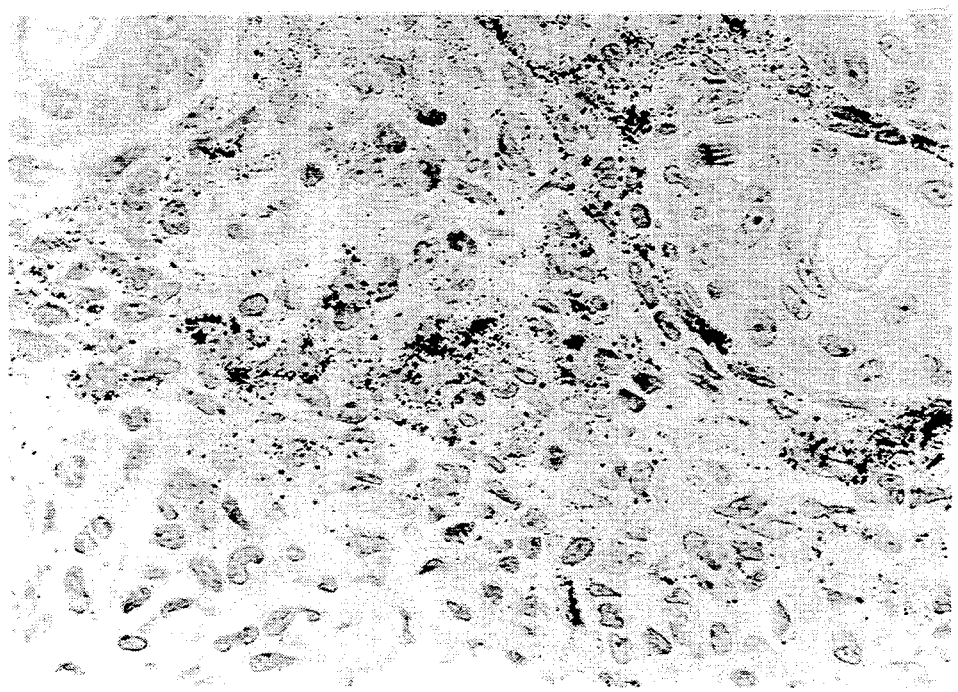
Figure 16C:

FIGS. 16A–16C show micrographs of tissue sections from experiments in which gold-containing liposomes were injected into psoriatic mice. FIG. 16C shows a low power (×400) micrograph of a section through a psoriatic lesion in which is apparent a concentration of silver-enhanced gold particles in the lesions around the psoriasis lesions between epidermis and dermis.

FIGS. 16A and 16B show higher power micrographs of the region, in which is apparent accumulation of silver-enhanced gold particles predominantly in the boundary of dermis region close to epidermis, and concentrated in the tip of papillae (FIG. 16A). In some early and developed lesions, inflammatory foci were highly proliferated with macrophages, polymorphonuclear leukocytes, and mast cells. Silver-enhanced colloidal gold was found scattered around these inflammatory cells. This can be seen in FIG. 16B. In addition, silver-enhanced gold particles were observed in regions surrounding hair follicles.

IV. Treatment of Inflamed Regions

As described above, liposomes of the invention are effective to localize and concentrate an entrapped therapeutic agent specifically in an inflamed region. Liposome compositions preferably have a relatively high drug carrying capacity and minimal leakage of the entrapped drug during the time required for the liposomes to distribute to and enter the inflamed region (the first 24–48 hours following injection in mice or rats). The liposomes thus provide an effective method for concentrating the liposome-entrapped therapeutic compound in an inflamed region. In accordance with the invention, the therapeutic compound is entrapped by such liposomes and the liposomal formulation is administered parenterally to a subject, preferably directly into the bloodstream.

In the context of the present invention, an inflamed site or region is generally a region anatomically at a site outside the bloodstream that is accessible from and adjacent a capillary bed. Inflamed regions which are most amenable to treatment by the method of the invention are characterized by an acute increase in permeability of the vasculature in the region of inflammation. In this case, for an IV injected liposome-entrapped therapeutic composition to reach the inflamed site, it must leave the bloodstream and enter the inflamed region. In one embodiment, the method of the invention is used to treat inflammation by concentrating an anti-inflammatory agent selectively in the inflamed region.

Therapeutic agents useful in the treatment of localized inflammation vary, according to the cause of the inflammation. Agents directed against the primary cause of the inflammation, such as infection, can be used in the treatment method. Commonly, general anti-inflammatory agents such as steroidal or non-steroidal anti-inflammatory agents will be used. More generally, the method of the invention includes a liposomal composition having an agent known to be useful in the treatment of a specific inflammatory state. By selectively localizing such therapeutic agents to inflamed regions, the method of the invention has the advantage over conventional drug regimens of decreased exposure of unaffected tissues to high doses of drug. This is expected to lower unwanted side effects of drug therapy.

The following discussion of exemplary inflammatory states and therapeutic agents useful in their treatment is intended to represent some of the types of inflammation which can be treated, using the treatment method described herein. This discussion is not intended to limit the scope of the invention, but is provided as a guide to the general applicability of the treatment method to states of inflammation. In general, a treatment regimen using liposomal preparations of the invention can be determined on the basis of knowledge of conventional therapeutic drugs and their effective concentration ranges for a particular disorder. Such information is available in standard medical reference guides such as Goodman (1990) or *The Physician's Desk Reference*. The method of the invention teaches determination of the amount of drug entrapped in a particular liposomal preparation and the percentage of such a preparation which is expected to be delivered to a site of inflammation. Such data provide basis for determination of an appropriate dose or dose range in an individual.

General antiinflammatory agents include, as noted above, steroids and non-steroids. Steroids commonly used as antiinflammatory agents include those corticosteroids having antiinflammatory effects greater than or equal to that of naturally occurring human cortisol (Haynes). Examples of antiinflammatory steroids given systemically include prednisone, methylprednisolone, paramethazone, 11-flurocortisol, triamcinolone, betamethasone and dexamethasone. Additionally, it is anticipated that certain antiinflammatory steroids, such as beclomethasone, which are conventionally administered only topically, due to their toxicity and/or high lipophilicity, will become available for systemic administration, in such liposomal compositions.

A number of inflammatory diseases and allergic reactions may be treated systemically with steroidal antiinflammatory agents; however due to the undesirable side effects of such agents, their prolonged use is generally reserved for particularly severe afflictions. Administration of systemic steroids is indicated for urticaria resulting from an undesirable immune reaction, multiple sclerosis, and organ implant. It is appreciated that these states can be advantageously be treated with liposome-entrapped steroidal compounds, and that such treatment is anticipated to reduce overall the dose of drug administered to the whole body and thereby to reduce unwanted side effects attributable to such drugs. Additionally, as discussed below, by reducing such systemic side effects, the method of the invention makes feasible treatment of diseases or conditions in which use of steroids was previously considered unwarranted or unadvisable, due to the relative severity of the state, relative to the side effects, and/or the length of treatment required. For example, long term use of adrenocorticosteroids for treatment of less severe cases of inflammation, such as for eczematous dermatitis, although considered beneficial, is not generally recommended, due to the side effects inherent in such systemic treatment regimens. Side effects associated with long term systemic adrenocorticosteroid usage include suppression of the hypothalamic-pituitary-adrenal axis (Cushing's syndrome), fluid and electrolyte disturbances, hypertension, peptic ulceration, osteoporosis, and myopathy.

Other agents generally useful in the treatment of inflammation include, but are not limited to free radical scavenging agents such as superoxide dismutase and nonsteroidal antiinflammatory drugs (NSAIDs), including, but not limited to salicylates (exemplified by aspirin), pyrazolon derivatives (exemplified by phenylbutazone), indomethacin, sulindac, tolmetin, fenamates (exemplified by meclofenamate), proprionic acid derivatives (exemplified by ibuprofen), oxicam derivatives (exemplified by piroxicam), phenylacetic acid derivatives (exemplified by diclofenac), etodolac, and nabumetone. Generally, although many of these drugs possess excellent antiinflammatory properties, side effects limit their use at doses effective to provide effective antiinflammatory treatment. In accordance with the invention, formulations of such drugs in liposomes having enhanced circulation times will are contemplated to provide selective relief of inflammation in subjects requiring such treatment. Other exemplary antiinflammatory agents are discussed with respect to specific indications, below.

Dermatological lesions are inflammations that may be caused by a number of local as well as systemic events, such as infections. Systemic administration of high doses of adrenocorticosteroids is currently considered appropriate therapy only for particularly severe chronic dermatoses, including pemphigus vulgaris, as well as in more acute severe dermatoses, such as allergic contact dermatitis. However, lesser disorders such as psoriasis, for which intralesional administration of corticosteroids is currently indicated, may also benefit from systemic administration of liposome-entrapped corticosteroids, as well as from liposomal therapies using antiproliferative drugs, immunosuppressive compounds such as cyclosporine A and selection (e.g., ELAM-1, GMP-140)-directed therapeutics, retinoids such as isotretinoin, and 5-fluorouracil.

The use of cyclosporine A in such dermatological inflammatory diseases as resistant psoriasis and atopic dermatitis is currently gaining favor. Poor absorption of cyclosporine topically necessitates systemic administration of the compound. In accordance with the present invention, liposomal formulations of cyclosporine are anticipated for such uses. Example 13 describes a method of producing such a cyclosporine liposomal formulation. Such formulations will also find use in other known clinical uses of cyclosporine, such as in organ transplant. Certain dermatological lesions associated with cancerous conditions, including Kaposi's sarcoma and T-cell lymphoma, may be treated with antiproliferative agents including vincristine and etoposide.

As described above, the liposomal compositions and treatment methods can be used to concentrate compounds to psoriatic lesions. In humans, psoriasis is a chronic condition which, although not life-threatening, can be debilitating. The precise cause of the disorder is unknown, though it has been suggested that neurogenic factors, including neuropeptides, are involved in its etiology (Pincelli). A number of therapeutic agents, including steroidal and non-steroidal antiinflammatory agents, antiproliferative agents (methotrexate, azaribine), immunosuppressants such as cyclosporine, and miscellaneous agents, such as etretinate, anthralin, psoralins and coal tar, are currently used in treatment of psoriasis. As described in Section III, above, liposomal compositions made in accordance with the invention are effective to localize and concentrate in psoriatic lesions. It is contemplated that similar liposomes, having entrapped antipsoriasis agents will be useful in treatment of psoriasis and other dermatological lesions.

Rheumatoid arthritis is an inflammatory condition in which steroid, as well as non-steroid therapeutics are useful treatments. NSAIDs, as described above, are also indicated in providing antiinflammatory relief in patients having arthritis (rheumatoid and osteoarthritis) and ankylosing spondylitis. Doses of NSAIDS required to provide pain relief are generally quite high, and are associated with significant side effects, including ulceration of the stomach and duodenum. Treatment with cyclosporine has also been found to be beneficial to sufferers of rheumatoid arthritis. Liposomal delivery of such drugs to inflamed regions, particularly joints, would be expected to reduce exposure of such susceptible regions. Other drugs useful in the treatment of arthritis include gold compounds (aurothioglucose, auranofin). These compounds may also reduce progression of the disease. Because they are bound by plasma proteins and sequestered by macrophages in a number of tissues, relatively high doses of such agents must be given to achieve therapeutic concentrations in affected regions (synovial fluid of joints). Such doses are associated with side effects, including blood dyscrasias, lesions of the mucous membranes, and chrysiasis. Such high doses are also relatively expensive. When given in liposome entrapped form, it is contemplated that lower doses of compound will be required, to achieve therapeutic concentrations in inflamed regions.

Gout, in its acute phase, is characterized as an inflammatory reaction to urate crystals present in joints, and includes local infiltrations of granulocytes. Acute phase symptoms of gout can be relieved by oral or intravenous administration of colchicine. Liposomal entrapment of this compound is expected to reduce serious side effects, such as agranulocytosis, associated with long-term treatment with the compound.

Neurogenic inflammation refers to a local tissue response elicited by stimulation of sensory nerves in a number of tissues. Commonly, susceptible organs include the eye, skin, joints and respiratory tract. In animal models of the respiratory tract, neurogenic inflammation is characterized by increased permeability of postcapillary venules and collecting venules in specific regions of the respiratory tract (McDonald). Systemic antiinflammatory therapy using the liposomal preparations of the invention is therefore expected to be useful in the delivery of therapeutic agents useful in the treatment of neurogenic inflammation.

Necrotizing vasculitides are diseases of the vascular system characterized by inflammation of the vascular system. These diseases, which may involve a variety of etiologies, are thought to have in common inappropriate immunologic reactions, as evidenced by the deposition of immune complexes in and around vessel walls. Examples of diseases which fall within the category of vasculitis include, but are not limited to, polyarteritis nodosa, serum sickness, Wegener's granulomatosis, and Kawasaki's syndrome (Kadison). Antiinflammatory steroids are indicated in many of these diseases. Therapy using the method of the invention is contemplated to be beneficial, as described above.

In summary, the present invention contemplates treatment of a variety of disorders which are either primarily inflammatory in presentation or which have as a component of their presentation, an inflammatory phase. Examples of disorders having inflammatory phases include adult respiratory distress syndrome, reperfusion injury following myocardial infarction and/or thrombolysis, septic shock, organ transplantation and diabetes.

The following examples illustrate, but in no way are intended to limit the present invention.

Materials and Methods

Materials

Cholesterol (Chol) was obtained from Sigma (St. Louis, Mo.) or from Calbiochem (La Jolla, Calif.). Sphingomyelin (SM), egg phosphatidylcholine (lecithin or PC), partially hydrogenated PC having the composition IV40, IV30, IV20, IV10, and IV1, phosphatidylglycerol (PG), phosphatidylethanolamine (PE), dipalmitoyl-phosphatidyl glycerol (DPPG), dipalmitoyl PC (DPPC), dioleyl PC (DOPC), distearoyl PC (DSPC) and egg PC were obtained from Avanti Polar Lipids (Alabaster, AL) or Austin Chemical Company (Chicago, Ill.). Distearyl phosphatidyl ethanolamine was obtained from Calbiochem (La Jolla, Calif.).

[$^{125}$I]-tyraminyl-inulin was made according to published procedures. $^{67}$Gallium-citrate was supplied by NEN Neoscan (Boston, Mass.). [$^{125}$I]gentamicin was from NEN (Cambridge, Mass.). Doxorubicin HCl and Epirubicin HCL were obtained from Adria Laboratories (Columbus, Ohio) or Farmitalia Carlo Erba (Milan, Italy).

Polyvinyl alcohol (PVA), glycolic acid, and lactic acid were from Aldrich (St. Louis, Mo.). Polylactic acid was supplied by ICN (Cleveland, Ohio).

All organic solvents used were reagent grade or high pressure liquid chromatography grade.

EXAMPLE 1

Preparation of PEG-PE Linked by Cyanuric Chloride

A. Preparation of activated PEG 2-0-Methoxypolyethyleneglycol1900-4,6-dichloro-1,3,5 triazine previously called activated PEG was prepared as described in J. Biol. Chem., 252: 3582 (1977) with the following modifications.

Cyanuric chloride (5.5 g; 0.03 mol) was dissolved in 400 ml of anhydrous benzene containing 10 g of anhydrous sodium carbonate, and PEG-1900 (19 g; 0.01 mol) was added and the mixture was stirred overnight at room temperature. The solution was filtered, and 600 ml of petroleum ether (boiling range, 35°-60°) was added slowly with stirring. The finely divided precipitate was collected on a filter and redissolved in 400 ml of benzene. The precipitation and filtration process was repeated several times until the petroleum ether was free of residual cyanuric chloride as determined by high pressure liquid chromatography on a column (250×3.2 mm) of 5-m "LiChrosorb" (E. Merck), developed with hexane, and detected with an ultraviolet detector. Titration of activated PEG-1900 with silver nitrate after overnight hydrolysis in aqueous buffer at pH 10.0, room temperature, gave a value of 1.7 mol of chloride liberated/mol of PEG.

TLC analysis of the product was carried out on TLC reversed-phase plates obtained from Baker using methanol/water, 4:1; v/v, as developer and exposure to iodine vapor for visualization. Under these conditions, the starting methoxy polyglycol 1900 appeared at $R_f$=0.54 to 0.60. The activated PEG appeared at $R_f$=0.41. Unreacted cyanuric chloride appeared at $R_f$=0.88 and was removed.

The activated PEG was analyzed for nitrogen and an appropriate correction was applied in selecting the quantity of reactant to use in further synthetic steps. Thus, when the product contained only 20% of the theoretical amount of nitrogen, the quantity of material used in the next synthetic step was increased by 100/20, or 5-fold. When the product contained 50% of the theoretical amount of nitrogen, only 100/50 or a 2-fold increase was needed.

B. Preparation of N-(4-Chloro-polyethyleneglycol 1900)-1,3,5-triazinyl Egg Phosphatidylethanolamine In a screw-capped test tube, 0.74 ml of a 100 mg/ml (0.100 mmole) stock solution of egg phosphatidylethanolamine in chloroform was evaporated to dryness under a stream of nitrogen and was added to the residue of the activated PEG described in section A, in the amount to provide 205 mg (0.100 mmole). To this mixture, 5 ml anhydrous dimethyl formamide was added. 27 microliters (0.200 mmole) triethylamine was added to the mixture, and the air was displaced with nitrogen gas. The mixture was heated overnight in a sand bath maintained at 110° C.

The mixture was then evaporated to dryness under vacuum and a pasty mass of crystalline solid was obtained. This solid was dissolved in 5 ml of a mixture of 4 volumes of acetone and 1 volume of acetic acid. The resulting mixture was placed at the top of a 21 mm×240 mm chromatographic absorption column packed with silica gel (Merck Kieselgel 60, 70–230 mesh) which had first been moistened with a solvent composed of acetone acetic acid, 80/20; v/v.

The column chromatography was developed with the same solvent mixture, and separate 20 to 50 ml aliquots of effluent were collected. Each portion of effluent was assayed by TLC on silica gel coated plates, using 2-butanone/acetic acid/water; 40/25/5; v/v/v as developer and iodine vapor exposure for visualization. Fractions containing only material of $R_f$= about 0.79 were combined and evaporated to dryness under vacuum. Drying to constant weight under high vacuum afforded 86 mg (31.2 micromoles) of nearly colorless solid N-(4-chloro-polyglycol 1900)-1,3,5-triazinyl egg phosphatidylethanolamine containing phosphorous.

The solid compound was taken up in 24 ml of ethanol/chloroform; 50/50 chloroform and centrifuged to remove insoluble material. Evaporation of the clarified solution to dryness under vacuum afforded 21 mg (7.62 micromoles) of colorless solid.

EXAMPLE 2

Preparation of Carbamate and Amide Linked Hydrophilic Polymers with PE

A. Preparation of the imidazole carbamate of polyethylene glycol methyl ether 1900

9.5 grams (5 mmoles) of polyethylene glycol methyl ether 1900 obtained from Aldrich Chemical Co. was dissolved in 45 ml benzene which has been dried over molecular sieves. 0.89 grams (5.5 mmoles) of pure carbonyl diimidazole was added. The purity was checked by an infra-red spectrum. The air in the reaction vessel was displaced with nitrogen. Vessel was enclosed and heated in a sand bath at 75° C. for 16 hours.

The reaction mixture was cooled and the clear solution formed at room temperature. The solution was diluted to 50.0 ml with dry benzene and stored in the refrigerator as a 100 micromole/ml stock solution of the imidazole carbamate of PEG ether 1900.

B. Preparation of the phosphatidylethanolamine carbamate of polyethylene glycol methyl ether 1900.

10.0 ml (1 mmol) of the 100 mmol/ml stock solution of the imidazole carbamate of polyethylene glycol methyl ether 1900 was pipetted into a 10 ml pear-shaped flask. The solvent was removed under vacuum. 3.7 ml of a 100 mg/ml solution of egg phosphatidyl ethanolamine in chloroform (0.5 mmol) was added. The solvent was evaporated under vacuum. 2 ml of 1,1,2,2-tetrachloroethylene and 139 microliters (1.0 mmol) of triethylamine VI was added. The vessel was closed and heated in a sand bath maintained at 95° C. for 6 hours. At this time, thin-layer chromatography was performed with fractions of the above mixture to determine an extent of conjugation on $SiO_2$ coated TLC plates, using butanone/acetic acid/water; 40/5/5; v/v/v; was performed as developer. Iodine vapor visualization revealed that most of the free phosphatidyl ethanolamine of $Rf=0.68$, had reacted, and was replaced by a phosphorous-containing lipid at $R_f=0.78$ to 0.80.

The solvent from the remaining reaction mixture was evaporated under vacuum. The residue was taken up in 10 ml methylene chloride and placed at the top of a 21 mm×270 mm chromatographic absorption column packed with Merck Kieselgel 60 (70–230 mesh silica gel), which has been first rinsed with methylene chloride. The mixture was passed through the column, in sequence, using the following solvents.

TABLE 1

| ml | Volume % of Methylene Chloride | Volume % Methylene with 2% Acetic Acid |
|---|---|---|
| 100 | 100% | 0% |
| 200 | 95% | 5% |
| 200 | 90% | 10% |
| 200 | 85% | 15% |
| 200 | 60% | 49% |

50 ml portions of effluent were collected and each portion was assayed by TLC on $SiO_2$-coated plates, using $I_2$ vapor absorption for visualization after development with chloroform/methanol/water/concentrated ammonium hydroxide; 130/70/8/0.5%; v/v/v/v. Most of the phosphates were found in fractions 11, 12, 13 and 14.

These fractions were combined, evaporated to dryness under vacuum and dried in high vacuum to constant weight. They yielded 669 mg of colorless wax of phosphatidyl ethanolamine carbamate of polyethylene glycol methyl ether. This represented 263 micromoles and a yield of 52.6% based on the phosphatidyl ethanolamine.

An NMR spectrum of the product dissolved in deuterochloroform showed peaks corresponding to the spectrum for egg PE, together with a strong singlet due to the methylene groups of the ethylene oxide chain at Delta=3.4 ppm. The ratio of methylene protons from the ethylene oxide to the terminal methyl protons of the PE acyl groups was large enough to confirm a molecular weight of about 2000 for the polyethylene oxide portion of the molecule of the desired product polyethylene glycol conjugated phosphatidyl-ethanolamine carbamate, M.W. 2,654.

C. Preparation of polylactic acid amide of phosphatidylethanolamine 200 mg (0.1 mmoles) poly (lactic acid), mol. wt.=2,000 (ICN, Cleveland, Ohio) was dissolved in 2.0 ml dimethyl sulfoxide by heating while stirring to dissolve the material completely. Then the solution was cooled immediately to 65° C. and poured onto a mixture of 75 mg (0.1 mmoles) of distearylphosphatidyl-ethanolamine (CalBiochem, La Jolla) and 41 mg (0.2 mmoles) dicyclohexyl-carbodiimide. Then 28 ml (0.2 mmoles) of triethylamine was added, the air swept out of the tube with nitrogen gas, the tube capped, and heated at 65° C. for 48 hours.

After this time, the tube was cooled to room temperature, and 6 ml of chloroform added. The chloroform solution was washed with three successive 6 ml volumes of water, centrifuged after each wash, and the phases separated with a Pasteur pipette. The remaining chloroform phase was filtered with suction to remove suspended distearylphosphatidyl ethanolamine. The filtrate was dried under vacuum to obtain 212 mg of semi-crystalline solid.

This solid was dissolved in 15 ml of a mixture of 4 volumes ethanol with 1 volume water and passed through a 50 mm deep and 21 mm diameter bed of $H^+$ Dowex 50 cation exchange resin, and washed with 100 ml of the same solvent. The filtrate was evaporated to dryness to obtain 131 mg colorless wax.

291 mg of such wax was dissolved in 2.5 ml chloroform and transferred to the top of a 21 mm×280 mm column of silica gel wetted with chloroform. The chromatogram was developed by passing through the column, in sequence, 100 ml each of:

100% chloroform, 0% (1% $NH_4OH$ in methanol);
90% chloroform, 10% (1% $NH_4OH$ in methanol);
85% chloroform, 15% (1% $NH_4OH$ in methanol);
80% chloroform, 20% (1% $NH_4OH$ in methanol);
70% chloroform, 30% (1% $NH_4OH$ in methanol).

Individual 25 ml portions of effluent were saved and assayed by TLC on $SFO_2$-coated plates, using $CHCl_3$, $CH_3OH$, $H_2O$, con. $NH_4OH$, 130, 70, 8, 0.5 v/v as developer and $I_2$ vapor absorption for visualization.

The 275–325 ml portions of column effluent contained a single material, $PO_4+$, of $R_f=0.89$. When combined and evaporated to dryness, these afforded 319 mg colorless wax. Phosphate analysis of the substance confirmed a molecular weight of about 115,000. This material was used to produce polylactic acid-PE containing liposomes used in experiments summarized in FIG. 10.

In this preparation, it appeared that the polymerization of the poly (lactic acid) occurred at a rate comparable to that at which it reacted with phosphatidylethanolamine. Minimization of this side-reaction could be achieved by using more dilute solutions of the reactants.

D. Preparation of polyglycolic acid amide of DSPE

A mixture of 266 mg. (3.50 mmoles) glycolic acid, 745 mg (3.60 mmoles) dicyclohexyl carbodiimide, 75 mg. (0.10 mmoles) distearoyl phosphatidyl ethanolamine, 32 microliters (0.23 mmoles triethyl amine, and 5.0 ml dry dimethyl sulfoxide was heated at 75° C., under a nitrogen atmosphere, cooled to room temperature, then diluted with an equal volume of chloroform, and then washed with three successive equal volumes of water to remove dimethyl sulfoxide. Phases were centrifuged and separated with a Pasteur pipette each time.

The chloroform phase was filtered under reduced pressure to remove a small amount of suspended material. The filtrate was then evaporated under vacuum to dryness to obtain 572 mg. pale amber wax. This material was redissolved in 2.5 ml chloroform and transferred to the top of a 21 mm×270 mm column of silica gel (Merck Kieselgel 60) previously wetted with chloroform.

The chromatogram was developed by passing through the column, in sequence, 100 ml each of:

100% chloroform, 0% (1% $NH_4OH$ in methanol);
90% chloroform, 10% (1% $NH_4OH$ in methanol);
85% chloroform, 15% (1% $NH_4OH$ in methanol);
80% chloroform, 20% (1% $NH_4OH$ in methanol);
70% chloroform, 30% (1% $NH_4OH$ in methanol).

Individual 25 ml portions of effluent were collected and assayed by TLC on $Si)_2$-coated plates, using $CHCl_3$, $CH_3OH$, $H_2O$, con-$NH_4OH$; 130, 70, 8, 0.5 v/v as developer. Almost all of the $PO_4$-positive material was found in the 275–300 ml portion of effluent. Evaporation of this portion to dryness under vacuum, followed by high-vacuum drying, afforded 281 mg of colorless wax. Phosphate analysis of the wax confirmed a molecular weight of 924,000. This material was used to produce polyglycolic acid-PE-containing liposomes used in experiments summarized in FIG. 10.

Manipulation of solvent volume during reaction and molar ratios of glycolic acid and dicyclohexyl carbodiimide produces compounds having different molecular weights.

E. Preparation of Polyglycolic/Polylactic Acid Amide of PE

The same synthetic approach detailed above can be applied to the preparation of random polylactic/polyglycolic copolymers chemically linked to PE by an amide bond. In this case, equimolar quantities of distearoyl phosphatidyl ethanolamine and a 1-to-1 mixture of polyglycolic acid, polylactic acid are mixed with a three-fold molar excess of dicyclohexyl carbodiimide and a two-fold molar excess of triethylamine in a sufficient volume of dimethyl sulfoxide to dissolve all components at 75° C. The reaction is allowed to proceed 48 hours under an inert atmosphere. The product is purified by column chromatography as described above for the polylactic and polyglycolic amides of PE.

F. Preparation of Polyvinyl Alcohol Carbamate of PE

Ten grams of 50,000 molecular weight polyvinyl alcohol (PVA) were dissolved in 200 ml water by heating. The solution was cooled to 45° C. and filtered. The solution was then mixed with an equal volume of acetone, and the resulting solid precipitate removed by filtration (Whatman #1). A low molecular weight (MW) PVA fraction was recovered from the filtrate by evaporation of the solvent. A yield of 920 mg was obtained.

PE was reacted with carbonyl diimidazole (CDI) in the presence of triethylamine (TEA) at a molar ratio of 1:1.1:1 (PE:CDI:TEA) in benzene at 75° C. for 4 hours. A low molecular weight fraction of PVA, prepared as detailed above, was then added (0.1 mole per mole of PE) and the reaction was continued at 75° C. for 24 hours. The resulting PVA-PE was used to prepare liposomes which were used in experiments summarized in FIG. 11.

EXAMPLE 3

Preparation of Ethylene-linked PEG-PE

A. Preparation of I-trimethylsilyloxy-polyethylene glycol

Preparation of I-trimethylsilyloxy-polyethylene glycol is illustrated in the reaction scheme shown in FIG. 3.

15.0 gm (10 mmoles) of polyethylene glycol M.Wt. 1500, (Aldrich Chemical) was dissolved in 80 ml benzene. 1.40 ml (11 moles) of chlorotrimethyl silane (Aldrich Chemical Co.) and 1.53 ml (1 mmoles) of triethylamine was added. The mixture was stirred at room temperature under an inert atmosphere for 5 hours.

The mixture was filtered with suction to separate crystals of triethylammonium chloride and the crystals were washed with 5 ml benzene. Filtrate and benzene wash liquids were combined. This solution was evaporated to dryness under vacuum to provide 15.83 grams of colorless oil which solidified on standing.

TLC of the product on Si-$C_{18}$ reversed-phase plates using a mixture of 4 volumes of ethanol with 1 volume of water as developer, and iodine vapor visualization, revealed that all the polyglycol 1500 ($R_f$=0.93) was consumed, and was replaced by a material of $R_f$=0.82. An infra-red spectrum revealed absorption peaks characteristic only of polyglycols.

Yield of I-trimethylsilyoxypolyethylene glycol, M.W. 1500 was nearly quantitative.

B. Preparation of trifluoromethane sulfonyl ester of I-trimethylsilyloxy-polyethylene glycol 15.74 grams (10 mmol) of the crystalline I-trimethylsilyloxy polyethylene glycol obtained above was dissolved in 40 ml anhydrous benzene and cooled in a bath of crushed ice. 1.53 ml (11 mmol) triethylamine and 1.85 ml (11 mmol) of trifluoromethanesulfonic anhydride obtained from Aldrich Chemical Co. were added and the mixture was stirred over night under an inert atmosphere until the reaction mixture changed to a brown color.

The solvent was then evaporated under reduced pressure and the residual syrupy paste was diluted to 100.0 ml with methylene chloride. Because of the great reactivity of trifluoromethane sulfonic esters, no further purification of the trifluoromethane sulfonyl ester of I-trimethylsilyloxy polyethylene glycol was done.

C. Preparation of N-1-trimethylsilyloxy polyethylene glycol 1500 PE 10 ml of the methylene chloride stock solution of the trifluoromethane sulfonyl ester of 1-trimethylsilyloxy polyethylene glycol was evaporated to dryness under vacuum to obtain about 1.2 grams of residue (approximately 0.7 mmoles). To this residue, 3.72 ml of a chloroform solution containing 372 mg (0.5 mmoles) egg PE was added. To the resulting solution, 139 microliters (1.0 mmole) of triethylamine was added and the solvent was evaporated under vacuum. To the obtained residue, 5 ml dry dimethyl formamide and 70 microliters (0.50 mmoles) triethylamine (VI) was added. Air from the reaction vessel was displaced with nitrogen. The vessel was closed and heated in a sand bath a 110° C. for 22 hours. The solvent was evaporated under vacuum to obtain 1.58 grams of brownish colored oil.

A 21×260 mm chromatographic absorption column filled with Kieselgel 60 silica 70–230 mesh, was prepared and rinsed with a solvent composed of 40 volumes of butanone, 25 volumes acetic acid and 5 volumes of water. The crude product was dissolved in 3 ml of the same solvent and transferred to the top of the chromatography column. The chromatogram was developed with the same solvent and sequential 30 ml portions of effluent were assayed each by TLC.

The TLC assay system used silica gel coated glass plates, with solvent combination butanone/acetic acid/water; 40/25/5; v/v/v. Iodine vapor absorption served for visualization. In this solvent system, the N-1-trimethylsilyloxy polyethylene glycol 1500 PE appeared at $R_f=0.78$. Unchanged PE appeared at $R_f=0.68$.

The desired N-1-trimethylsilyloxy polyethylene glycol 1500 PE was a chief constituent of the 170–300 ml portions of column effluent. When evaporated to dryness under vacuum these portions afforded 111 mg of pale yellow oil of compound.

D. Preparation of N-polyethylene glycyl 1500: Phosphatidylethanolamine Acetic Acid Deprotection Once-chromatographed, PE compound was dissolved in 2 ml of tetrahydrofuran. To this, 6 ml acetic acid and 2 ml water was added. The resulting solution was let to stand for 3 days at 23° C. The solvent from the reaction mixture was evaporated under vacuum and dried to constant weight to obtain 75 mg of pale yellow wax. TLC on Si-C18 reversed-phase plates, developed with a mixture of 4 volumes ethanol, 1 volume water, indicated that some free PE and some polyglycol-like material formed during the hydrolysis.

The residue was dissolved in 0.5 ml tetrahydrofuran and diluted with 3 ml of a solution of ethanol water; 80:20; v:v. The mixture was applied to the top of a 10 mm×250 mm chromatographic absorption column packed with octadecyl bonded phase silica gel and column was developed with ethanol water 80:20% by volume, collecting sequential 20 ml portions of effluent. The effluent was assayed by reversed phase TLC. Fractions containing only product of Rf=0.08 to 0.15 were combined. This was typically the 20–100 ml portion of effluent. When evaporated to dryness, under vacuum, these portions afforded 33 mg of colorless wax PEG-PE corresponding to a yield of only 3%, based on the starting phosphatidyl ethanolamine.

NMR analysis indicated that the product incorporated both PE residues and polyethylene glycol residues, but that in spite of the favorable-appearing elemental analysis, the chain length of the polyglycol chain has been reduced to about three to four ethylene oxide residues. The product prepared was used for a preparation of PEG-PE liposomes.

E. Preparation of N-Polyethylene Glycol 1500 P.E. by Fluoride Deprotection.

500 mg of crude N-1-trimethylsilyloxy polyethylene glycol PE was dissolved in 5 ml tetrahydrofuran and 189 mg (0.600 millimoles) of tetrabutyl ammonium fluoride was added and agitated until dissolved. The reactants were let to stand over night at room temperature (20° C.).

The solvent was evaporated under reduced pressure and the residue was dissolved in 10 ml chloroform, washed with two successive 10 ml portions of water, and centrifuged to separate chloroform and water phases. The chloroform phase was evaporated under vacuum to obtain 390 mg of orange-brown wax, which was determined to be impure N-polyethylene glycol 1500 PE compound.

The wax was re-dissolved in 5 ml chloroform and transferred to the top of a 21×270 mm column of silica gel moistened with chloroform. The column was developed by passing 100 ml of solvent through the column. The Table 2 solvents were used in sequence.

TABLE 2

| Volume % Chloroform | Volume % Methanol Containing 2% Conc. Ammonium Hydroxide/Methanol |
|---|---|
| 100% | 0% |
| 95% | 5% |
| 90% | 10% |
| 85% | 15% |
| 80% | 20% |
| 70% | 30% |
| 60% | 40% |
| 50% | 50% |
| 0% | 100% |

Separated 50 ml fractions of column effluent were saved. The fractions of the column were separated by TLC on Si-C18 reversed-phase plates. TLC plates were developed with 4 volumes of ethanol mixed with 1 volume of water. Visualization was done by exposure to iodine vapor.

Only those fractions containing an iodine-absorbing lipid of $R_f$ about 0.20 were combined and evaporated to dryness under vacuum and dried in high vacuum to constant weight. In this way 94 mg of waxy crystalline solid was obtained of M.W. 2226. The proton NMR spectrum of this material dissolved in deuterochloroform showed the expected peaks due to the phosphatidyl ethanolamine portion of the molecule, together with a few methylene protons attributable to polyethylene glycol. (Delta=3.7).

EXAMPLE 4

Preparation of REVs and MLVs

A. Sized REVs

A total of 15 μmoles of the selected lipid components, in the mole ratios indicated in the examples below, were dissolved in chloroform and dried as a thin film by rotary evaporation. This lipid film was dissolved in 1 ml of diethyl ether washed with distilled water. To this lipid solution was added 0.34 ml of an aqueous buffer solution containing 5 mM Tris, 100 mM NaCl, 0.1 mM EDTA, pH 7.4, and the mixture was emulsified by sonication for 1 minute, maintaining the temperature of the solution at or below room temperature. Where the liposomes were prepared to contain encapsulated [$^{125}$I] tyraminyl-inulin, the compound was included in the phosphate buffer at a concentration of about 4 μCi/ml buffer.

The ether solvent was removed under reduced pressure at room temperature, and the resulting gel was taken up in 0.1 ml of the above buffer, and shaken vigorously. The resulting REV suspension had particle sizes, as determined by microscopic examination, of between about 0.1 to 20 microns, and was composed predominantly of relatively large (greater than 1 micron) vesicles having one or only a few bilayer lamellae.

The liposomes were extruded twice through a polycarbonate filter (Szoka, 1978), having a selected pore size of 0.4 microns or 0.2 microns. Liposomes extruded through the 0.4 micron filter averaged 0.17±(0.05) micron diameters, and through the 0.2 micron filter, 0.16±(0.05) micron diameters. Non-encapsulated [$^{125}$I] tyraminyl-inulin was removed by passing the extruded liposomes through Sephadex G-50 (Pharmacia).

B. Sized MLVs

Multilamellar vesicle (MLV) liposomes were prepared according to standard procedures by dissolving a mixture of lipids in an organic solvent containing primarily CHCl$_3$ and drying the lipids as a thin film by rotation under reduced pressure. In some cases a radioactive label for the lipid phase was added to the lipid solution before drying. The lipid film was hydrated by addition of the desired aqueous phase and 3 mm glass beads followed by agitation with a vortex and shaking above the phase transition temperature of the phospholipid component for at least 1 hour. In some cases a radioactive label for the aqueous phase was included in the buffer. In some cases the hydrated lipid was repeatedly frozen and thawed three times to provide for ease of the following extrusion step.

MLVs having specific compositions were produced by the method described below.

1. MLV Method 1

Multilamellar vesicles were prepared by hydrating either of two solid lipid mixture forms: thin film or lyophilized tertbutanol solution. Lipid mixtures were prepared with one or more of the following: partially hydrogenated egg phosphatidylcholine (PHEPC) with an iodine value of 40 (Asahi Chemical, Japan) hydrogenated soy phosphatidylcholine (HSPC) (Avanti Polar Lipids, Alabaster, Ala.), USP grade cholesterol (C) (Croda), N-carbamyl-poly(ethylene glycol methyl ether)-1,2-distearyl-sn-glycero-3-phospho-ethanolamine, sodium salt (MPEG-1900-DSPE) (Chemsyn, Lenexa, Kans.). Thin films of lipids were hydrated by shaking with the component. The resulting liposomes dispersions were frozen and thawed three times before further processing. Lyophilized lipid mixtures were hydrated by shaking with the aqueous phase as above. Extrusion was performed under high pressure in a stainless steel cell (MICO, Middleton, Wis.) through successively smaller defined pore filters until a pore size of 0.05 μm diameter was reached (Nucleopore, Pleasanton, Calif.) or a mean particle diameter of less than or equal to 100 nm. The particle size distribution was determined by dynamic light scattering (Coulter N4SD). Phospholipid concentrations were measured by phosphorus determination (Bartlett, 1959). In some cases, the lipids were hydrated by slowly pouring ethanol lipid solutions into an aqueous solution above the phase transition temperature of the phospholipid component and shaking for 60 min. These dispersions were homogenized with a Rannie Minilab-8 (St. Paul, Minn.) above the phase transition temperature of the phospholipid component at pressures sufficient to give a mean particle diameter of less than or equal to 100 nm. In one case, the homogenization pressure was reduced to yield a sample with a mean particle diameter of 150 nm.

PEG-containing liposomes typically had a composition comprising PEG-DSPE:HSPC:Cho=0.15:1.85:1, representing a PEG-DSPE content of 5 mole percent, unless otherwise indicated.

C. Loading of Labeled Compounds into Liposomes

1. $^{67}$Ga-DF-labeled Liposomes

The protocol for preparation of $^{67}$Ga-DF labeled liposomes as adapted from known procedures (Gabizon, 1988-1989). Briefly, REV or MLV liposomes were prepared as described above. The ion chelator desferal mesylate (DF) was encapsulated in the internal aqueous phase of the liposomes and used to irreversibly trap $^{67}$Ga-DF in the liposome.

$^{67}$Ga-citrate for injection (Neoscan, NEN Cambridge Mass.) is supplied as a 2 mCi/ml solution. Conversion of the citrate chelate to a bilayer permeable oxide chelate (hydroxyquinoline) was performed by diluting the Ga-citrate stock 1:10 with 5 mg/ml hydroxyquinoline sulfate (Sigma Chemical Co.) in 0.9% saline for injection and heating to 50° C. for 1 hr. The heating step was performed on a 1-2 ml solution in a capped and sealed 15 ml conical test tube in a lead shipping container placed on a hot plate and filled with about 2 ml of water. After heating, the Ga-oxide stock solution was allowed to cool and stored at room temperature in a lead shipping container.

For $^{67}$Ga-DF loading of liposomes, samples were hydrated with desferoxamine mesylate (DF, Sigma Chemical, St. Louis, Mo.) in the buffer. Unentrapped DF was removed by either dialysis or gel permeation chromatography. Gel permeation chromatography was performed on columns pre-equilibrated with the buffer but lacking DF. The samples were then mixed 10:1 with the Ga-oxide solution and then capped, mixed, and incubated at 4° C. Loading with 0.1-3 μCi/μM lipid gave good results. Unentrapped Ga label was removed by either dialysis or gel chromatography.

2. Colloidal Gold Liposomes

A solution of citric acid (120 mM) and K$_2$CO$_3$ (30 mM) was freshly prepared and mixed with gold tetrachloride (HAuCL$_4$; 12.72 mM) in a ratio of 1:1, pH 3.4. Liposomes composed of either PC/C/G$_{M1}$ (molar ratio 10:5:1), or PC/C/PEG-DSPE (molar ratio 10:5:1) were prepared by reverse-phase evaporation (Szoka) with gold chloride/citrate in the aqueous phase (Huang). A thin lipid film (10 μmol phospholipid) was dissolved in 1 ml of diethyl ether, and mixed with 0.5 ml gold chloride/citrate solution. The mixture was emulsified for 3 minutes in a bath sonicator, and diethyl ether was removed under vacuum at room temperature. The liposomes underwent three cycles of freezing and thawing, and then were extruded under pressure (Olson) through Nucleopore membranes (Pleasanton, Calif.), twice through pore-size 0.1 μm and five times through 0.05 μm. Immediately after final extrusion, the pH of the liposome suspension was raised to 6 by adding NaOH. It was then incubated at 55° C. for 30 minutes. The color of the liposome suspension turned pink-purple, which indicated an appropriate particle size. After gold particles had formed, unencapsulated free gold and excess citrate were removed by passing the liposome suspension through a column (1×15 cm) of Sephacryl S-500 (Pharmacia, Piscataway, N.J.). The average size of the liposomes was 80-100 nm diameter determined by electron microscopy. The percentage of liposomes containing gold as determined by negative stain electron microscopy (Huang) was between 60-90, varying among preparations. Most of them contain more than one gold particle. The gold-liposomes were stable during 2 weeks storage under argon at 4° C. In vivo, gold-containing liposomes remain intact in the blood stream, the relative ratio of gold-containing and plain liposomes recovered in plasma at 24 h after i.v. injection in mice was almost the same as before injection (Huang).

3. Rhodamine-Labeled Liposomes

Sized REVs were prepared as described in Examples 4A, above. The liposome composition was PC/Chol/PEG-DSPE/Rho-PE in molar ratio of 10:5:0.8:0.1. Rhodamine-PE was incorporated as one of the lipids in the composition.

D. Determination of Liposome Particle Size Distribution by Dynamic Light Scattering Liposome particle size distribution measurements were obtained by DLS using a NICOMP Model 200 with a Brookhaven Instruments BI-2030AT autocorrelator attached, or with a Coulter N4SD. The instruments were operated according to the manufacturer's instructions. The NICOMP results were expressed as the mean diameter and standard deviation of a Gaussian distribution of vesicles by relative volume.

EXAMPLE 5

Liposome Blood Lifetime Measurements

A. Measuring Blood Circulation Time and Blood/RES Ratios

In vivo studies of liposomes were performed in two different animal models: Swiss-Webster mice at 25 g each and laboratory rats as 200–300 g each. The studies in mice involved tail vein injection of liposome samples at 1 μM phospholipid/mouse followed by animal sacrifice after a defined time and tissue removal for label quantitation in a scintillation counter. The weight and percent of the injected dose in each tissue were determined. The studies in rats involved establishment of a chronic catheter in a femoral artery for removal of blood samples at defined times after injection of liposome samples in a catheter in the other femoral vein at 3–4 μM phospholipid/rat. Alternatively, liposome samples were administered to the tail vein and bold samples obtained by retro-orbital bleeding. In general, rat studies were carried out using $^{67}$Ga-DF loaded liposomes and radioactivity was measured using a gamma counter. The percent of the injected dose remaining in the blood at several time points up to 24 hours, and in selected tissues at 24 hours, was determined.

B. Time Course of Liposome Retention in the Bloodstream

PEG-PE composed of methoxy PEG, molecular weight 1900 and PEG-DSPE was prepared as in Example 2. The PEG-DSPE lipid was combined with and partially hydrogenated egg PC (PHEPC) in a lipid:lipid mole ratio of about 0.1:2, and the lipid mixture was hydrated and extruded through a 0.1 micron polycarbonate membrane, as described in Example 4, to produce MLV's with average size about 0.1 micron. The MLV lipids included a small amount of radiolabeled lipid marker $^{14}$C-cholesteryl oleate, and the encapsulated marker, $^3$H-inulin or $^{67}$Ga-DF, as described in Example 4.

The liposome composition was injected and the percent initial injected dose in mice was determined at 1, 2, 3, 4, and 24 after injection. The time course of loss of radiolabeled material is seen in FIG. 7 which is a plot of percent injected dose for encapsulated inulin (solid circles), inulin marker corrected to the initial injection point of 100% (open circles), and lipid marker (closed triangles), over a 24-hour period post injection. As seen, both lipid and encapsulated markers showed greater than 10% of original injected dose after 24 hours.

C. 24 Hour Blood Liposome Levels

Studies to determine percent injected dose in the blood, and blood/RES ratios of a liposomal marker, 24 hours after intravenous liposome injection, were carried out as described above. Liposome formulations having the compositions shown at the left in Table 3 below were prepared as described above. Unless otherwise noted, the lipid-derivatized PEG was PEG-1900, and the liposome size was 0.1 micron. The percent dose remaining in the blood 24 hours after intravenous administration, and 24-hour blood/RES ratios which were measured are shown in the center and right columns in the table, respectively.

TABLE 3

| Lipid Composition* | 24 Hours after IV Dose | |
|---|---|---|
| | % Injected Dose in Blood | B/RES |
| PG:PC:Chol (.75:9.25:5) | 0.2 | 0.01 |
| PC:Chol (10:5) | 0.8 | 0.03 |
| PEG-DSPE:PC:Chol | 23.0 | 3.0 |
| PEG-DSPE:PC:Chol (250 nm) | 9.0 | 0.5 |
| PEG$_{5000}$-DSPE:PC:Chol | 21.0 | 2.2 |
| PEG$_{750}$-DSPE:PC:Chol | 3.2 | 0.3 |
| PEG$_{120}$-DSPE:PC:Chol | 5.0 | 0.2 |
| PEG-DSPE:PC (0.75:9.25) | 22.0 | 1.7 |
| PEG-DSPE:PG:PC:Chol (0.75:2.25:7:5) | 40.0 | 4.0 |
| PEG-DSPE:NaCholSO$_4$:PC:Chol (0.75:0.75:9.25:4.25) | 25.0 | 2.5 |

*All formulations contain 33% cholesterol and 7.5% charged component and were 100 nm mean diameter except as noted. PEG-DSPE consisted of PEG $_{1900}$ except as noted. Liposome distribution and kinetics were followed using encapsulated $^{67}$Ga-DF as a label. Rates were injected IV as described in Example 4.

As seen, percent dose remaining in the blood 24 hours after injection ranged between 5–40% for liposomes containing PEG-derivatized lipids. By contrast, in both liposome formulations lacking PEG-derivatized lipids, less than 1% of liposome marker remained after 24 hours. Also as seen in Table 3, blood/RES ratios increased from 0.01–0.03 in control liposomes to at least 0.2, and as high as 4.0 in liposomes containing PEG-derivatized liposomes.

D. Blood Lifetime Measurements with Polylactic Acid Derivatized PE

Figure 10:
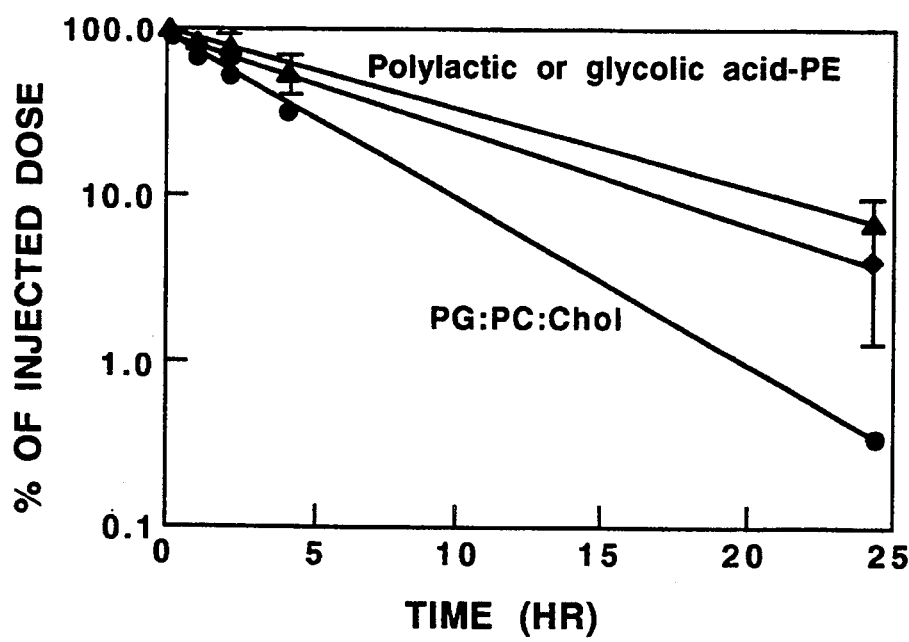
FIG. 10 is a plot similar to that of FIG. 7, showing the blood residence time of polylactic or polyglycolic acid-coated liposomes (solid triangles; upper line) and conventional uncoated liposomes (solid circles; lower line)

Studies to determine percent injected dose in the blood at several times after intravenous liposome injection were carried out as described above. Typical results with extruded MLV liposome formulation having the composition Polylactic Acid-PE:HSPC:Chol at either 2:3.5:1 or 1:3.5:1 weight % is shown in FIG. 10 (solid squares). The percent dose remaining normalized at 15 min. is shown over 24 hours.

These data indicate that the clearance of the polylactic acid-coated liposomes is severalfold slower than similar formulations without polylactic acid derivatized PE.

E. Blood Lifetime Measurements with Polyglycolic Acid Derivatized PE

Studies to determine percent injected dose in the blood at several times after intravenous liposome injection were carried out as described above. Typical results with extruded MLV liposome formulation having the composition Polyglycolic Acid-PE:HSPC:Chol at 2:3.5:1 weight % are shown in FIG. 10 (open triangles).

The percent dose remaining normalized at 15 min. is shown over 24 hours.

These data indicate that the clearance of the polyglycolic acid-coated liposomes is severalfold slower than similar formulations without polyglycolic acid derivatized PE.

F. Blood Lifetime Measurements with Polyvinyl Alcohol PE

Figure 11:
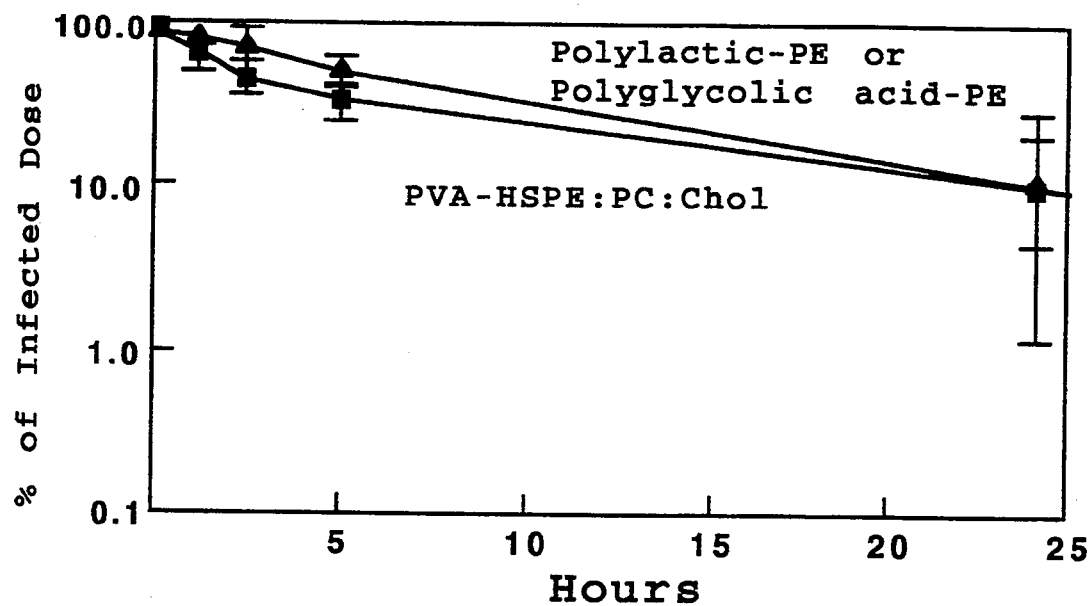
FIG. 11 is a plot similar to that of FIG. 7, showing the blood residence time of polylactic or polyglycolic acid-coated liposomes (upper line) and polyvinyl alcohol-coated liposomes (lower line)

Studies to determine percent injected dose in the blood at several times after intravenous liposome injection were carried out as described above. Typical results with extruded MLV liposome formulation having the composition Polyvinyl alcohol-HSPE:PC:Chol at either 2:3.5:1 or 1:3.5:1 weight % is shown in FIG. 11 in comparison to the results of polylactic acid- and polyglycolic acid-derivatized liposomes described in Sections E and F, above. The percent dose remaining normalized at 15 min. is shown over 24 hours. The results for blood residence time of polyvinyl alcohol-derivatized liposomes are similar to results obtained for polylactic acid- and polyglycolic acid-derivatized species, as described above. These data indicate that the clearance of the polyvinyl alcohol-coated liposomes is severalfold slower than similar formulations without polyvinyl alcohol derivatized PE.

EXAMPLE 6

Effect of Phospholipid Acyl-Chain Saturation on Blood/RES Ratios in PEG-PE Liposomes PEG-PE composed of methoxy PEG, molecular weight 1900 and distearyl PE (DSPE) was prepared as in Example 2. The PEG-PE lipids were formulated with selected lipids from among sphingomyelin (SM), fully hydrogenated soy PC (PC), cholesterol (Chol), partially hydrogenated soy PC (PHSPC), and partially hydrogenated PC lipids identified as PC IV1, IV10, IV20, IV30, and IV40 in Table 4. The lipid components were mixed in the molar ratios shown at the left in Table 5, and used to form MLV's sized to 0.1 micron as described in Example 4.

TABLE 4

| Egg PC Form | Phase Transition Temperature Range °13 C. | Mole % Fatty Acid Comp. | | | | | |
|---|---|---|---|---|---|---|---|
| | | 18:0 | 18:1 | 18:2 | 20:0 | 20:1–4 | 22:1–6 |
| Native | <0 | 12 | 30 | 15 | 0 | 3 | 05 |
| IV 40 | <0 | 14 | 32 | 4 | 0 | 3 | 04 |
| IV 30 | <20–30 | 20 | 39 | 0 | 1 | 2 | 34 |
| IV 20 | 23–45 | 30 | 10 | 0 | 2 | 1 | 33 |
| IV 10 | 37–50 | 42 | 4 | 0 | 3 | 1 | 42 |
| IV 1 | 49–54 | 56 | 0 | 0 | 5 | 0 | 60 |

TABLE 5[a]

| | Blood | RES | B/RES | % Remaining |
|---|---|---|---|---|
| PEG-PE:SM:PC:Chol 0.2:1:1:1 | 19.23 | 6.58 | 2.92 | 49.23 |
| PEG-PE:PHSPC:Chol 0.15:1.85:1 | 20.54 | 7.17 | 2.86 | 55.14 |
| PEG-PE:PC IV1:Chol 0.15:1.85:1 | 17.24 | 13.71 | 1.26 | 60.44 |
| PEG-PE:PC IV1:Chol (two animals) 0.15:1.85:1 | 19.16 | 10.07 | 1.90 | 61.87 |
| PEG-PE:PC IV10:Chol (two animals) 0.15:1.85:1 | 12.19 | 7.31 | 1.67 | 40.73 |
| PEG-PE:PC IV10:Chol 0.15:1.85:1 | 2.4 | 3.5 | 0.69 | [b]12.85 |
| PEG-PE:PC IV20:Chol 0.15:1.85:1 | 24.56 | 7.52 | 3.27 | 62.75 |
| PEG-PE:PC IV40:Chol 0.15:1.85:1 | 5.2 | 5.7 | 0.91 | [b]22.1 |
| PEG-PE:PC IV40:Chol 0.15:1.85:1 | 19.44 | 8.87 | 2.19 | 53.88 |
| PEG-PE:PC IV:Chol 0.15:1.85:0.5 | 20.3 | 8.8 | 2.31 | 45.5 |
| PEG-PE:EPC:Chol 0.15:1.85:1 | 15.3 | 9.6 | 1.59 | 45.9 |

[a]Groups of at least 3 mice were used per experiment except where otherwise noted and $^{67}$Ga-DF was used to follow the liposomes.
[b]Values with low recoveries (i.e., <40%) are considered unreliable.

Twenty-four hours after injection, the percent material injected (as measured by percent of $^{\delta}$Ga-DF) remaining in the blood and in the liver (L) and spleen (S) were determined, and these values are shown in the two data columns at the left in Table 5. The blood and L+S (RES) values were used to calculate a blood/RES value for each composition. The column at the right in Table 5 shows total amount of radioactivity recovered. The two low total recovery values in the table indicate anomalous clearance behavior.

The results from the table demonstrate that the blood/RES ratios are largely independent of the fluidity, or degree of saturation of the phospholipid components forming the liposomes. In particular, there was no systematic change in blood/RES ratio observed among liposomes containing largely saturated PC components (e.g., IV1 and IV10 PC's), largely unsaturated PC components (IV40), and intermediate-saturation components (e.g., IV20).

In addition, a comparison of blood/RES ratios obtained using the relatively saturated and relatively compounds (Example 5) indicates that the degree of saturation of the derivatized lipid is itself not critical to the ability of the liposomes to evade uptake by the RES.

EXAMPLE 7

Effect of Cholesterol and Ethoxylated Cholesterol on Blood/RES Ratios in PEG-PE Liposomes

A. Effect of Added Cholesterol

Methoxy PEG, molecular weight 1900 and was derivatized with DSPE as described in Example 2. The PEG-PE lipids were formulated with selected lipids from among sphingomyelin (SM), fully hydrogenated soy PC (PC), and cholesterol (Chol), as indicated in the column at the left in Table 6 below. The three formulations shown in the table contain about 30, 15, and 0 mole percent cholesterol. Both REV's (0.3 micron size) and MLV's (0.1 micron size) were prepared, substantially as in Example 4, with encapsulated tritium-labeled inulin.

The percent encapsulated inulin remaining in the blood 2 and 24 hours after administration, given at the left in Table 6 below, show no measurable effect of cholesterol, in the range 0–30 mole percent.

TABLE 6

| | % Injected Dose in Blood | | | |
|---|---|---|---|---|
| | 2 hr. | 24 hr. | 2 hr. | 24 h. |
| | $^3$H Aqueous Label (Leakage) | | $^{14}$C-Lipid Label | |
| $^3$H-Inulin | | | | |
| SM:PC:Chol:PEG-DSPE | | | | |

TABLE 6-continued

| $^3$H-Inulin | % Injected Dose in Blood | | | |
|---|---|---|---|---|
| | 2 hr. $^3$H Aqueous Label (Leakage) | 24 hr. | 2 hr. $^{14}$C-Lipid Label | 24 h. |
| 1:1:1:0.2 | | | | |
| 100 nm MLV | 19 | 5 | 48 | 24 |
| 300 nm REV | 23 | 15 | 67 | 20 |
| SM:PC:Chol:PEG-DSPE 1:1:0.5:0.2 | | | | |
| 300 nm REV | 23 | 15 | 71 | 17 |
| SM:PC:PEG-DSPE 1:1:0.2 | | | | |
| 100 nm MLV | 19 | 6 | 58 | 24 |
| 300 nm REV | 32 | 23 | 76 | 43 |

B. Effect of Ethoxylated Cholesterol

Methoxy-ethoxy-cholesterol was prepared by coupling methoxy ethanol to cholesterol via the trifluorosulfonate coupling method described in Section I. PEG-PE composed of methoxy PEG, molecular weight 1900 and was derivatized DSPE as described in Example 2. The PEG-PE lipids were formulated with selected lipids from among distearyl-PC (DSPC), partially hydrogenated soy PC (HSPC), cholesterol, and ethoxylated cholesterol, as indicated at the left in Table 7. The data show that (a) ethoxylated cholesterol, in combination with PEG-PE, gives about the same degree of enhancement of liposome lifetime in the blood as PEG-PE alone. By itself, the ethoxylated cholesterol provides a moderate degree of enhancement of liposome lifetime, but substantially less than that provided by PEG-PE.

TABLE 7

| Formulation | % Injected Dose in Blood $^{14}$C-Chol-Oleate | |
|---|---|---|
| | 2 hr. | 24 hr. |
| HSPC:Chol:PEG-DSPE 1.85:1:0.15 | 55 | 9 |
| HSPC:Chol:PEG-DSPE:PEG$_5$-Chol 1.85:0.85:0.15:0.15 | 57 | 9 |
| HSPC:Chol:HPG:PEG$_5$-Chol 1.85:0.85:0.15:0.15 | 15 | 2 |
| HSPC:Chol:HPG 1.85:1:0.15 | 4 | 1 |

C. Effect of High Cholesterol Content on Blood/RES Ratios in PEG-PE Liposomes Methoxy PEG, molecular weight 1900 was derivatized with DSPE as described in Example 2. The PEG-PE lipids were formulated with lipids selected from among distearoyl PC (DSPC) and cholesterol (Chol), prepared as MLV's, sized to 0.1 micron as in Example 4. The liposomal formulations were used in experiments summarized in FIG. 9, where liposomes containing about 5 mole percent cholesterol (solid circles) or 50 mole percent cholesterol (solid squares) were compared to conventional liposomes lacking PEG (open circles).

The percent of injected liposome dose present 0.25, 1, 2, 4, and 24 hours after injection are plotted for all formulations in FIG. 9. As seen, the percent cholesterol in the composition had little or no effect on liposome retention in the bloodstream. The slight increase in liposome retention observed for the high (50 mole percent) cholesterol liposomes may be attributable to a slower rate of loss of encapsulated marker.

EXAMPLE 8

Effect of Charged Lipid Components on Blood/RES Ratios in PEG-PE Liposomes

Methoxy PEG, molecular weight 1900 was derivatized with DSPE as described in Example 2. The PEG-PE lipids were formulated with lipids selected from among egg PG (PG), partially hydrogenated egg PC (PHEPC), and cholesterol (Chol), prepared as MLV's, sized to 0.1 micron as in Example 4. The two liposomal formulations were used in experiments summarized in FIG. 7, where liposomes containing about 4.7 mole percent (triangles) or 14 mole percent (circles) were compared.

The percent of injected liposome dose present 0.25, 1, 2, 4, and 24 hours after injection are plotted for both formulations in FIG. 7. As seen, the percent PG in the composition had little or no effect on liposome retention in the bloodstream. The rate of loss of encapsulated marker seen is also similar to that observed for similarly prepared liposomes containing no PG.

EXAMPLE 9

Plasma Kinetics of PEG-Coated and Uncoated Liposomes

Methoxy PEG, molecular weight 1900 and distearyl-PE (DSPE) were prepared as in Example 2. The PEG-PE lipids were formulated with PHEPC, and cholesterol, in a mole ratio of 0.15:1.85:1. A second lipid mixture contained the same lipids, but without PEG-PE. Liposomes were prepared from the two lipid mixtures as described in Example 5, by lipid hydration in the presence of desferal mesylate, followed by sizing to 0.1 micron, and removal of non-entrapped desferal by gel filtration with subsequent loading of $^{67}$Ga-oxide into the liposomes. The unencapsulated $^{67}$Ga was removed during passage through a Sephadex G-50 gel exclusion column. Both compositions contained 10 μmoles/ml in 0.15M NaCl, 0.5 mM desferal.

The two liposome compositions (0.4 ml) were injected IV in animals, as described in Example 6. At time 0.25, 1, 3 or 5 and 24 hours after injection, blood samples were removed and assayed for amount inulin remaining in the blood, expressed as a percentage of the amount measured immediately after injection. The results are shown in FIG. 8B. As seen, the PEG-coated liposomes have a blood halflife of about 11 hours, and nearly 30% of the injected material is present in the blood after 24 hours. By contrast, uncoated liposomes showed a halflife in the blood of less than 1 hour. At 24 hours, the amount of injected material was undetectable (FIG. 8B).

EXAMPLE 10

Extravasation of Liposomes into Sites of Bradykinin-Induced Inflammation

A. Rat Skin Flap Model

Rats were prepared having a dorsal skin flap window chamber for induction of inflammation by topical application of bradykinin (Papenfuss, et al., 1979).

Albumin (bovine serum; BSA) conjugated to fluorescein isothiocyanate (FITC) was obtained from Molecular Probes, Eugene, Oreg. Unconjugated BSA was from Sigma (St. Louis, Mo.). Fluorescently labeled (rhodamine) liposomes were composed of PC/Chol/PEG-DSPE/Rho-PE in molar ratio of 10:5:0.8:0.1. They were prepared as described in Example 4. The liposomes used in these experiments were approximately 80–95 nm in diameter.

Fluorescently tagged (FITC) BSA (dose: 40 mg/ml, 0.15 cc) and rhodamine-liposomes (dose: 10 μmole phospholipid/ml; 0.1 ml) were co-injected into a rat having a skin flap window, as described above. Light intensity of emission fluorescence was measured from the interstitial and vascular spaces in the region of the skin flap window. Excitation and emission frequencies used were as follows: 494 and 520 nm for FITC-BSA; 546 and 590 nm for Rholiposomes, respectively. Bradykinin solution (1 μM) was applied directly into the window chamber of the rat skin flap model following removal of one side of glass, and light emission was monitored continuously, as shown in FIG. 12A (using approximately 5 nM BSA) and FIG. 13A (using approximately 90 nm liposomes), in which emission light intensity in vascular (solid triangles) and interstitial regions (solid squares) was measured before and after bradykinin application. Sharp increases in fluorescence attributable to BSA-associated label and to liposome-associated label were observed in the interstitial region just after application of bradykinin, as indicated. Visual assessment of the regions confirmed the accumulation of liposomes in the interstitial region, by the presence of bright spots therein following bradykinin treatment. Such visually apparent fluors were not observed prior to the application of bradykinin to the region.

These data were converted to a plot of averaged permeability constants (FIG. 12B and FIG. 13B), calculated according to the permeability equation (Wu, 1991) and shown as fluorescence intensity Y in the figures, as a function of time (X). As plotted, permeability is proportional to the slope, $\alpha$, of the plot of Y vs. X. A 10-fold increase in vascular permeability to albumin was observed following bradykinin treatment. Permeability to liposomes was essentially zero, prior to bradykinin application. Permeability of ~90 nm liposomes was about ⅓ that of approximately 5 nM albumin following bradykinin treatment and about 4 times that of albumin measured subsequent to bradykinin treatment.

Figure 14A:
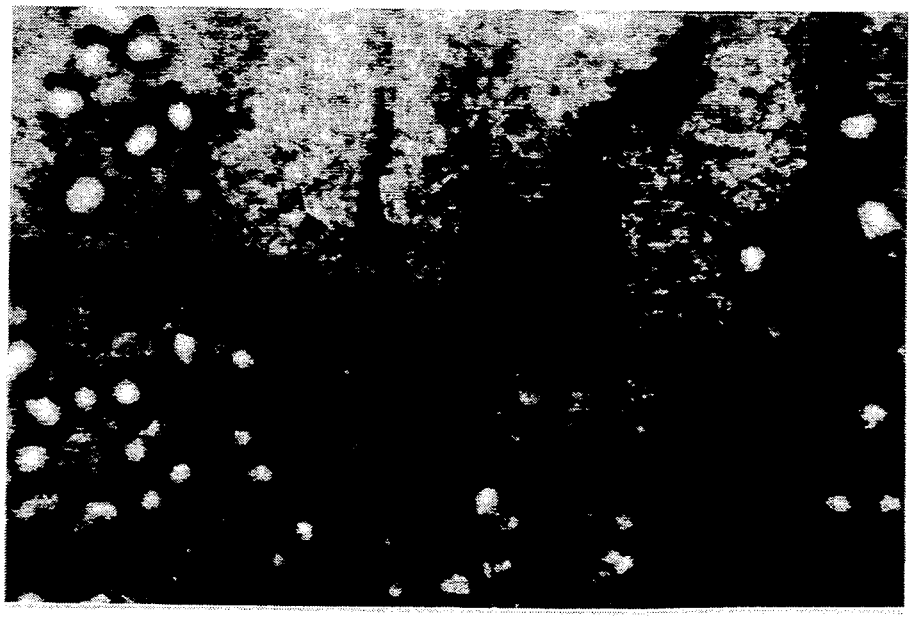
FIGS. 14A–14E show micrographs of vasculature from the dorsal flap window preparation in which images of the microvasculature are shown using transmitted light (14A), fluorescent emission immediately after intravenous injection of Rhodamine-labeled liposomes (14B), fluorescent emission from rhodamine-labeled liposomes 30 minutes after bradykinin treatment (14C), fluorescent image immediately after intravenous injection of fluorescein labeled-albumin (14D), and 30 minutes after albumin injection (14E)
Figure 14B:
Figure 14C:
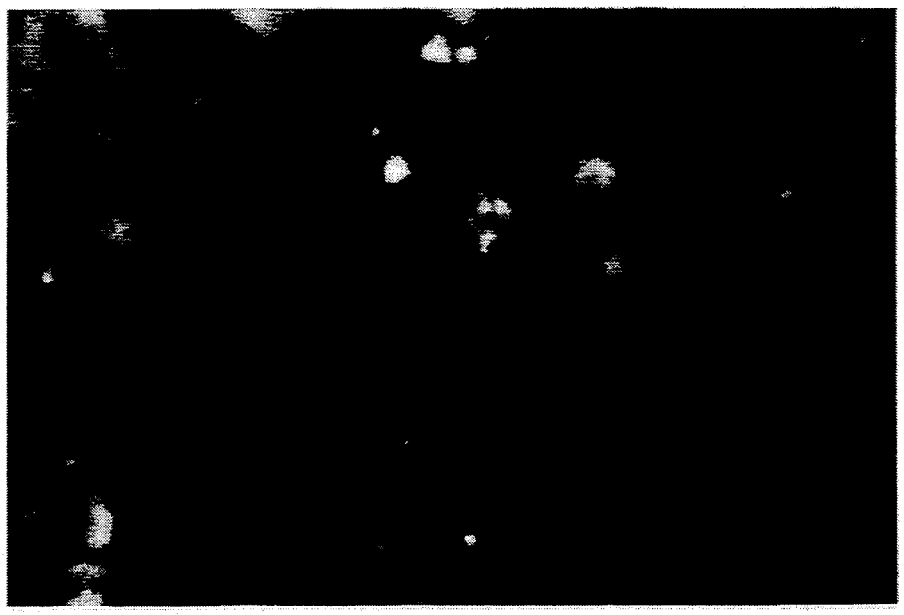
Figure 14D:
Figure 14E:
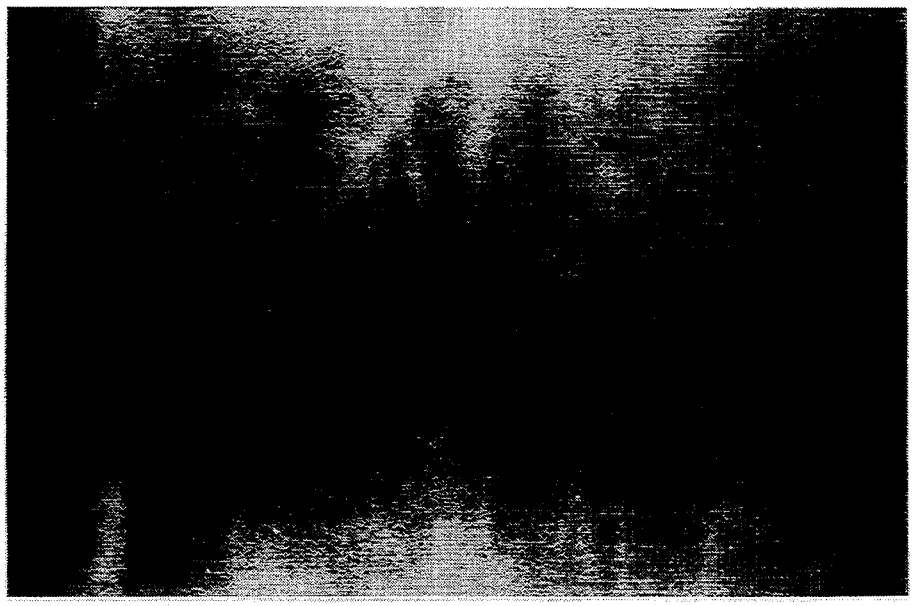

Micrographs of vasculature from the dorsal flap window preparation before and after treatment with bradykinin are shown in FIGS. 14A–E. FIG. 14A shows the microvasculature in transmitted light. FIG. 14B shows fluorescence image immediately after intravenous injection of Rhodamine labeled-liposomes. FIG. 14C is a fluorescence image of rhodamine-labeled liposomes in the region obtained 30 minutes after bradykinin treatment. Several leakage sites at vessels are shown (bright areas) by extravasation of Rhodamine labeled-liposomes. Extrusion of FITC-labeled albumin is also seen after bradykinin treatment (comparing FIG. 14D to FIG. 14E).

EXAMPLE 11

Extravasation of Colloidal Gold-Labeled Liposomes into Psoriatic Lesions

A. Animals Models

Mice, strain FSN, with single gene immunologic mutants were obtained from Dr. Leonard D. Shultz, the Jackson Laboratory. They developed dermal lesions resembling human psoriasis (Sundberg, et al.), as shown in FIG. 15. Some of the mice showed visible nude patches on the skin.

B. Injection of Gold-labeled Liposomes and Tissue Processing

Colloidal gold-containing liposomes (0.25 ml, 2 μmol phospholipid) were injected into mice having the psoriatic lesions described above via the tail vein. The mice were sacrificed 24 hours after liposome injection. Tissues were collected following perfusion with heparinized PBS and fixative (1.5% glutaraldehyde, 0.1M Na cacodylate, 1% sucrose, pH 7.4).

The tissue specimens were embedded in water-soluble JB-4 resin, from Polysciences, Inc., Warrington, Pa. All procedures involving tissue handling were performed at 4° C. Sections were cut from embedded specimens with a Sorvall JB-4 microtome at a thickness of 2.5 μm.

Reagents A (enhancer) and B (initiator) for silver enhancement were purchased from Amersham (Arlington Heights, Ill.). The sample area on the slide was covered with mixture (A and B) for 15 minutes at 22° C. The thin sections were stained with hematoxylin for 1 minute and Eosin Y (1%) for 15 minutes. Sections were examined by light microscopy. FIGS. 16A–16C show micrographs from these experiments.

EXAMPLE 12

Preparation of Steroidal Liposome Suspension

A lipid mixture containing PEG-DSPE (4–6 mole %), cholesterol sulfate (30–60 mole %), cholesterol (20–50 mole %), beclomethasone dipropionate (10 mole %) in amounts of 40 μmole/ml per liposomal formulation is dissolved in 10 ml methanol:chloroform (2:1), added to a screw-cap test tube and dried under nitrogen. The procedure is repeated three times and the dried film is lyophilized for half an hour at room temperature. Depending on the liposomal volume needed, the residue is resuspended in about 2 to 5 ml of phosphate buffered saline and sonicated with a bath sonicator (Model G112SP1T, 600 volts, 80 KC, 0.05 Amps) for half an hour to prepare multilamellar vesicles (MLVs) as detailed in Example 4. An aliquot of the sonicated, perextruded MLVs sample is saved and volume of preparation recorded by determination of baseline values. The suspension is extruded with a succession of Nucleopore polycarbonate membranes to produce liposomes in the size range of 0.07–0.2 μm in diameter, as described in Example 4.

A post-extrusion sample is saved to determine the amount of drug or lipid lost in the sizing process. Post-extrusion volume is noted. Free drug, if any, is removed by repeated washing with phosphate buffered saline and centrifugation. Liposomes are centrifuged three times on the Beckman L8-70M Ultracentrifuge at a temperature of 4° C., at 47,600 rpm, for 1 hour, using 50 Ti rotor. The supernatant is discarded and the pellet resuspended in a volume equal to the post-extrusion volume after each centrifugation.

EXAMPLE 13

Preparation of Cyclosporine-Containing Liposomes

Liposomes are prepared using the conventional film method (Example 4) with the drug included in the lipid film. PEG-DSPE (4–6 mole %), PC or negative charged lipids such as PG (40–60 mole %), chol (25–30 mole %), and positive charged lipids such as stearyamine (10–20 mole %) are mixed with cyclosporine A powder (2–3 mole %) in a round-bottom flask and dissolved in a chloroform/methanol solution (1:2). After evaporating to dryness under vacuum at room temperature followed by flushing with $N_2$ gas, liposomes are prepared by shaking the dried lipid film vigorously with phosphate buffered saline (pH 7.4) at room temperature for 30 minutes under $N_2$. After four freezing and thawing cycles, the liposomes are extruded under pressure (Olson) through a stack of two Nucleopore membranes (Pleasanton, Calif.) (0.2 μm pore size twice, 0.1 μm pore size twice and 0.05 μm pore size 7 times). Resulting liposomes are approximately 80–100 nm in diameter. Free drug, if any, is removed by repeated washing with phosphate buffered saline and centrifugation in a Beckman L8-70M Ultracentrifuge at 45,000 rpm, 4° C., for 1 hour, using a 50 Ti rotor.

The final liposomal drug concentration is determined by spectrophotometry at 405 nm. Cyclosporine-containing liposomes are administered intravenously through the mouse tail vein. Blood and tissue cyclosporine A concentrations are determined by the fluorescence polarization immunoassay (Abbott Laboratories, N. Chicago, Ill.) using HPLC.

While the invention has been described with reference to specific methods and embodiments, it will be appreciated that various modifications and changes may be made without departing from the invention.

It is claimed:

1. A method of concentrating a therapeutic compound in an inflamed dermal region in a subject, comprising administering to the subject, by parenteral injection, a composition of liposomes (i) composed of vesicle-forming lipids including an amphipathic vesicle-forming lipid derivatized with a hydrophilic biocompatible polymer selected from the group consisting of a polyethylene glycol having a molecular weight between about 300 and 5,000 daltons, polyglycolic acid (PGA), polylactic acid (PLA), a copolymer of PGA and PLA, and polyvinyl alcohol (ii) having a selected mean particle diameter in the size range between about 0.07–0.20 microns, and (iii) containing in liposome-entrapped form, a therapeutic compound effective against the source of the inflammation, and by said injecting, concentrating the liposomes in the inflamed region, thereby to concentrate liposome-entrapped compound at the site of inflammation.

2. The method of claim 1, wherein the liposome-entrapped compound is a steroidal anti-inflammatory compound.

3. The method of claim 2, wherein the anti-inflammatory compound is selected from the group consisting of prednisone, methylprednisolone, paramethazone, 11-fludrocortisol, triamcinolone, betamethasone and dexamethasone.

4. The method of claim 2, wherein the antiinflammatory compound is beclomethasone.

5. The method of claim 1, wherein the dermal inflammation is a psoriatic dermal inflammation, and the liposome-entrapped compound is selected from the group consisting of steroidal antiinflammatory agents, nonsteroidal antiinflammatory agents, immunosuppressant agents, methotrexate, azaribine, etretinate, anthralin, and psoralins.

6. The method of claim 5, wherein the immunosuppressant agent is cyclosporine.

* * * * *